(12) United States Patent
Hu et al.

(10) Patent No.: US 7,642,245 B2
(45) Date of Patent: *Jan. 5, 2010

(54) ANTIBACTERIAL COMPOUNDS HAVING A (PYRROLE CARBOXAMIDE)-(BENZAMIDE)-(IMIDAZOLE CARBOXAMIDE) MOTIF

(75) Inventors: Wenhao Hu, North Brunswick, NJ (US); Roland W. Burli, Pasadena, CA (US)

(73) Assignee: Oscient Pharmaceuticals Corporation, Waltham, MA (US)

( * ) Notice: Subject to any disclaimer, the term of this patent is extended or adjusted under 35 U.S.C. 154(b) by 101 days.

This patent is subject to a terminal disclaimer.

(21) Appl. No.: 11/518,503

(22) Filed: Sep. 8, 2006

(65) Prior Publication Data

US 2007/0142268 A1   Jun. 21, 2007

Related U.S. Application Data

(63) Continuation of application No. 10/732,900, filed on Dec. 9, 2003, now Pat. No. 7,129,214.

(60) Provisional application No. 60/432,465, filed on Dec. 10, 2002.

(51) Int. Cl.
A61K 38/00 (2006.01)
A01N 43/42 (2006.01)

(52) U.S. Cl. .................................. 514/18; 514/307

(58) Field of Classification Search ........................ None
See application file for complete search history.

(56) References Cited

U.S. PATENT DOCUMENTS

| | | | |
|---|---|---|---|
| 3,622,574 A | 11/1971 | Wright et al. | |
| 4,738,980 A | 4/1988 | Arcamone et al. | |
| 4,766,142 A | 8/1988 | Arcamone et al. | |
| 4,800,211 A | 1/1989 | Tischler et al. | |
| 4,912,199 A | 3/1990 | Lown et al. | |
| 5,017,599 A | 5/1991 | Lazzari et al. | |
| 5,049,579 A | 9/1991 | Lazzari et al. | |
| 5,310,752 A | 5/1994 | Lazzari et al. | |
| 5,350,748 A | 9/1994 | Boschelli et al. | |
| 5,395,849 A | 3/1995 | Wittman et al. | |
| 5,472,976 A | 12/1995 | Animati et al. | |
| 5,502,068 A | 3/1996 | Lown et al. | |
| 5,545,640 A | 8/1996 | Beaulieu et al. | |
| 5,616,606 A | 4/1997 | Lown et al. | |
| 5,670,534 A | 9/1997 | Animati et al. | |
| 5,698,674 A | 12/1997 | Bruice et al. | |
| 5,753,629 A | 5/1998 | Beria et al. | |
| 5,801,155 A | 9/1998 | Kutyavin et al. | |
| 5,808,087 A | 9/1998 | Matsunaga et al. | |
| 5,821,258 A | 10/1998 | Matsunaga | |
| 5,844,110 A | 12/1998 | Gold | |
| 5,852,011 A | 12/1998 | Matsunaga et al. | |
| 5,998,140 A | 12/1999 | Dervan et al. | |
| 6,090,947 A | 7/2000 | Dervan et al. | |
| 6,143,901 A | 11/2000 | Dervan | |
| 6,153,642 A | 11/2000 | Cozzi et al. | |
| 6,172,104 B1 | 1/2001 | Tidwell et al. | |
| 6,458,768 B1 | 10/2002 | Cozzi et al. | |
| 6,555,693 B2 | 4/2003 | Ge et al. | |
| 6,566,393 B1 | 5/2003 | Lee et al. | |
| 6,586,561 B1 | 7/2003 | Litt et al. | |
| 6,716,866 B2 | 4/2004 | McMinn et al. | |
| 6,777,425 B2 * | 8/2004 | Burli et al. | 514/307 |
| 6,825,228 B2 * | 11/2004 | Burli et al. | 514/422 |
| 7,129,214 B2 * | 10/2006 | Hu et al. | 514/18 |
| 2003/0199516 A1 * | 10/2003 | Moser et al. | 514/252.02 |
| 2003/0211508 A1 | 11/2003 | Ge et al. | |
| 2003/0236198 A1 * | 12/2003 | Burli et al. | 514/19 |
| 2005/0004042 A1 | 1/2005 | Hu et al. | |

FOREIGN PATENT DOCUMENTS

| | | |
|---|---|---|
| DE | 199 20 936 A1 | 11/2000 |
| GB | 2 310 207 A | 2/1996 |
| JP | 08-027146 A | 10/1996 |
| JP | 08-269008 A | 10/1996 |
| JP | 11-171886 A | 6/1999 |
| JP | 11-189594 A | 7/1999 |
| WO | WO 92/13838 A1 | 8/1992 |
| WO | WO 93/13739 A2 | 7/1993 |
| WO | WO 94/20463 A1 | 9/1994 |
| WO | WO 95/24419 A1 | 9/1995 |
| WO | WO 96/26950 A1 | 9/1996 |

(Continued)

OTHER PUBLICATIONS

Dyatkina, N.B., et al "Minor groove DNA binders as antimicrobial agents. 1. Pyrrole tetraamides are potent antibacterials against vancomycin resistant Enterococci [corrected] and methicillin resistant *Staphylococcus aureus*," J Med Chem. Feb. 14, 2002;45(4):805-17.*

(Continued)

*Primary Examiner*—Cecilia Tsang
*Assistant Examiner*—Thomas S Heard
(74) *Attorney, Agent, or Firm*—Townsend and Townsend and Crew LLP

(57) ABSTRACT

Compounds of the formula (I)

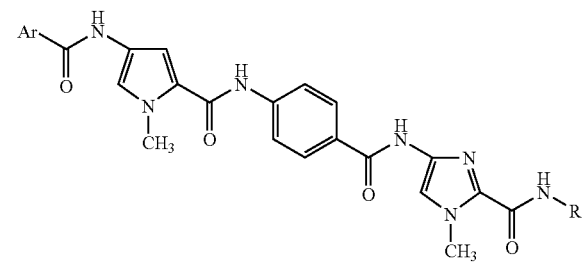

where Ar and R are as defined herein, possess antibacterial properties.

1 Claim, 11 Drawing Sheets

FOREIGN PATENT DOCUMENTS

| | | |
|---|---|---|
| WO | WO 97/03957 A1 | 2/1997 |
| WO | WO 97/25351 A2 | 7/1997 |
| WO | WO 97/28123 A1 | 8/1997 |
| WO | WO 98/21202 A1 | 5/1998 |
| WO | WO 98/35702 A1 | 8/1998 |
| WO | WO 98/37066 A1 | 8/1998 |
| WO | WO 98/37067 A1 | 8/1998 |
| WO | WO 98/37087 A1 | 8/1998 |
| WO | WO 98/43663 A1 | 10/1998 |
| WO | WO 98/45284 A1 | 10/1998 |
| WO | WO 98/49142 A1 | 11/1998 |
| WO | WO 98/50582 A1 | 11/1998 |
| WO | WO 98/52614 A2 | 11/1998 |
| WO | WO 99/00364 A1 | 1/1999 |
| WO | WO 99/25686 A1 | 5/1999 |
| WO | WO 99/27939 A1 | 6/1999 |
| WO | WO 99/41367 A1 | 8/1999 |
| WO | WO 99/50265 A1 | 10/1999 |
| WO | WO 99/50266 A1 | 10/1999 |
| WO | WO 99/62890 A1 | 12/1999 |
| WO | WO 99/64413 A1 | 12/1999 |
| WO | WO 00/06541 A1 | 2/2000 |
| WO | WO 00/06542 A1 | 2/2000 |
| WO | WO 00/15209 A2 | 3/2000 |
| WO | WO 00/15773 A2 | 3/2000 |
| WO | WO 00/40605 A2 | 7/2000 |
| WO | WO 00/69432 A1 | 11/2000 |
| WO | WO 01/10439 A1 | 2/2001 |
| WO | WO 01/19792 A1 | 3/2001 |
| WO | WO 01/21615 A1 | 3/2001 |
| WO | WO 01/74898 A2 | 10/2001 |
| WO | WO 01/96313 A1 | 12/2001 |
| WO | WO 02/00650 A2 | 1/2002 |
| WO | WO 02/088119 A1 | 11/2002 |
| WO | WO 02/101073 A2 | 12/2002 |
| WO | WO 2004/012736 A1 | 2/2004 |

OTHER PUBLICATIONS

Arcamone, F. et al., "Synthesis, DNA binding and antiviral activity of distamycin analogues containing different heterocyclic moieties." *Anti-Cancer Drug Design*, 1:235-244 (1986).

Bailly, C. and J.B. Chaires, "Sequence-specific DNA minor groove binders. Design and synthesis of netropsin and distamycin analogues." *Bioconj. Chem.*, 9(5):513-538 (1998).

Baird, E.E. and P.B. Dervan, "Solid phase synthesis of polyamides containing imidazole and pyrrole amino acids." *J. Am. Chem. Soc.*, 118:6141-46 (1996).

Baraldi et al., "Synthesis of 3-Substituted-7-alkoxy-5H-pyrazolo [4,3-d],2,3-triazin-4(3H)-ones" *Synthesis*, pp. 1437-1440, (1994), XP002208604.

Baraldi, P.G. et al., "Synthesis and antitumor activity of new benzoheterocyclic derivatives of distamycin A." *J. Med. Chem.*, 43:2675-2684 (2000).

Berge, S.M., et al, "Pharmaceutical Salts", *J. Pharm. Sci.*, 66:1-19 (1977).

Bilder G. et al., "Restenosis following angioplasty in the swine coronary artery is inhibited by an orally active PDGF-receptor tyrosine kinase inhibitor, RPR101511A." *Circulation*, 99(25):3292-99 (1999).

Boger, D.L. et al., "A simple, high-resolution method for establishing DNA binding affinity and sequence selectivity." *J. Am. Chem. Soc.*, 123:5878-91 (2001).

Boger, D.L. et al., "Total synthesis of distamycin A and 2640 analogues: A solution-phase combinatorial approach to the discovery of new bioactive DNA binding agents and development of a rapid high-throughput screen for determining relative DNA binding affinity or DNA binding sequence selectivity." *J. Am. Chem. Soc.*, 122:6382-94 (2000).

Bremer, R.E. et al., "Recognition of the DNA minor groove by pyrrole-imidazole polyamides: comparison of desmethyl-and n-methylpyroole." *Bioorg. Med. Chem.*, 8:1947-55 (2000).

Bruice, Thomas C. et al., "Rational design of substituted tripyrrole peptides that complex with DNA by both selective minor-groove binding and electrostatic interaction with the phosphate backbone." *Proc. Natl. Acad. Sci. USA*, 89:1700-04 (1992).

Chiarino, D. et al., "Synthesis of new isoxazole aminoalcohols." *J. Heterocyclic Chem.*, 25(1):337-342 (1988).

Choudhury, G.G. et al., "Involvement of PKC-alpha in PDGF-mediated mitogenic signaling in human mesangial cells." *Am. J. Physiol.*, 265(5 Pt 2):F634-42 (1993).

Corallini, A. et al. "Characterization of the effects of two polysulfonated distamycin A derivatives, PNU145156E and PNU153429, on HIV type 1 Tat protein." *AIDS Res. Hum. Retroviruses*, 4(17):1561-71 (1998).

Dyatkina, N.B. et al., "Minor groove DNA binders as antimicrobial agents. 1. Pyrrole tetraamides are potent antibacterials against vancomycin resistant Enterococci [corrected] and methicillin resistant *Staphylococcus aureus*." *J. Med. Chem*.; 45(4):805-17 (2002).

Ellervik, U. et al., "Hydroxybenzamide/pyrrole pair distinguishes T•A from A•T base pairs in the minor groove of DNA" *J. Am. Chem. Soc.* 122(39):9354-60 (2000).

El-Naggar, A.M. et al., "Synthesis of some 2-thenoyl-, 5-bromo-2-thenoyl- and 5-nitro-2-thenoylamino acid derivatives and their antimicrobial activity." *J. Indian Chem. Soc.*, LIX:783-786 (1982).

Fenwick et al., "Solid-phase synthesis of cyclic alkoxyketones, inhibitors of the cysteine protease cathepsin K." *Bioorg. Med. Chem. Lett.*, 11:195-98 (2001).

Floreancig, P.E. et al., "Recognition of the minor groove of DNA by hairpin polyamides containing alpha-substituted-beta-amino acids." *J. Am. Chem. Soc.*, 122:6342-50 (2000).

Goodsell D. and R.E. Dickerson, "Isohelical analysis of DNA groove-binding drugs." *J. Med. Chem.*, 29(5):727-33 (1986).

Gougerot-Pocidalo, M.A. et al. "Mechanisms by which oxidative injury inhibits the proliferative response of human lymphocytes to PHA. Effect of the thiol compound 2-mercaptoethanol." *Immunology*; 64(2):281-8 (1988).

Gupta et al., "Hybrid molecules containing propargylic sulfones and DNA minor groove-binding lexitropsins: synthesis, sequence specificity of reaction with DNA and biological evaluation." *Gene*, 149:81-90 (1994).

Handler, J.A. et al., "Mitogenic signaling by epidermal growth factor (EGF), but not platelet-derived growth factor, requires arachidonic acid metabolism in BALB/c 3T3 cells. Modulation of EGF-dependent c-myc expression by prostaglandins." *J. Biol. Chem.*, 265(7):3669-73 (1990).

Heldin C.H. and B. Westermark, "Mechanism of action and in vivo role of platelet-derived growth factor." *Physiol. Rev.*; 79(4):1283-316 (1999).

Herman, D.M. et al., "Cycle Polyamide Motif for Recognition of the Minor Groove of DNA." *J. Am. Chem. Soc.*, 121(6):1121-29 (1999).

Kelly, J.J. et al., "Binding site size limit of the 2:1 pyrrole-imidazole polyamide-DNA motif." *Proc. Natl. Acad. Sci. USA*, 93:6981-85 (1996).

Khalaf, A.I. et al., "The synthesis of some head to head linked DNA minor groove binders." *Tetrahedron*, 56:5225-39 (2000).

Kopka, M.L. et al., "Defining GC-specificity in the minor groove: side-by-side binding of the di-imidazole lexitropsin to C-A-T-G-G-C-C-A-T-G." *Structure*, 5(8)1033-46 (1997).

Machon, Z. and S. Ryng, "Synthesis and biological properties of 5-benzoylamino-3-methyl-4-isoxazolocarboxylic acid derivatives." *Arch. Immunol. Ther. Exp. (Warsz).*, 29(6):813-21 (1981).

Matsuba, Y. et al., "A novel synthetic DNA minor groove binder, MS-247: antitumor activity and cytotoxic mechanism." *Cancer Chemo. Pharm.*, 46:1-9 (2000).

Matsumoto, T. et al., "Synthesis of sulfonamido oligo-N-methylpyrrole-carboxamide derivatives and their photochemical DNA cleaving activities." *Heterocycles*, 33(1):135-138 (1992).

Matusomoto, T. et al. "Synthesis of halogenated oligo-N-methylpyrrole-carboxamide derivatives and their photochemical DNA cleaving activities." *Heterocycles*, 34(9):1697-1702 (1992).

Mrksich, M. et al., "Hairpin peptide motif, a new class of oligopeptides for sequence-specific recognition in the minor groove of double-helical DNA." *J. Am. Chem. Soc.*, 116:7983-88 (1994).

Neidle, S., "DNA minor-groove recognition by small molecules." *Nat. Prod. Rep.*, 18:291-309 (2001).

Nguyen, J.T. et al. "Exploiting the basis of proline recognition by SH3 and WW domains: design of N-substituted inhibitors." *Science*, 282(5396):2088-92 (1998).

Nielsen, P.E. "Sequence-Selective DNA Recognition by Synthetic Ligands." *Bioconjug. Chem.*, 2(1):1-12 (1991).

Pae, A.N. et al., "Synthesis and in vitro activity of new oxazolidinone antibacterial agents having substituted isoxazoles", *Bioorg. Med. Chem. Lett.*, 9:2679-84 (1999).

Plescia, S. et al., "3α-hydroxysteroid dehydrogenase inhibitory activity of some N(3)-(1-R-4-carboxypyrazol-5-yl)-1,2,3-benzotriazin-4(3H)-one and quinazoline-4(3H)-one acids." *Il Farmaco*, 49(7,8):505-07 (1994).

Plouvier, B. et al., "DNA-sequence specific recognition by a thiazole analogue of netropsin: a comparative footprinting study." *Nucl. Acids Res.*, 19(21):5821-5829 (1991).

Rao, K.E. et al., "Interaction of synthetic analogues of distamycin and netropsin with nucleic acids. Does curvature of ligand play a role in distamycin-DNA interactions?" *Biochemistry*, 27(8):3018-24 (1988).

Rao, K.E. et al., "Molecular recognition between oligopeptides and nucleic acids: DNA sequence specificity and binding properties of thiazole-lexitropsins incorporating the concepts of base site acceptance and avoidance." *Anti-Cancer Drug Design*, 5:3-20 (1990).

Renkema, G.H. and K. Saksela, "Interactions of HIV-1 NEF with cellular signal transducing proteins." *Frontiers in Bioscience*, 5:d268-83 (2000).

Sakai, Y. et al., "Synthesis of halogenated thiazole derivatives of oligo-N-methylpyrrolecarboxamide and their photochemical DNA cleaving activities." *Heterocycles*, 36(3):565-73 (1993).

Sen et al., "Synthesis of Compounds Related to Reserpine Skeleton." *J. Indian Chem. Soc.*, 46(3):209-15, also in *Chemical Abstracts* 71(1):318 (1969).

Sharma et al., "Design and Synthesis of Novel Thiazole-Containing Cross-Linked Polyamides Related to the Antiviral Antibiotic Distamycin." *J. Org. Chem*, p. est: 5.3 (1999).

Tanis, Steven P. and David B. Head, "Furans in synthesis. The preparation of (.+-.)-lactaral", *Tetrahedron Lett.*, 23:(52) pp. 5509-5512 (1982).

Taylor, J.S. et al., "DNA affinity cleaving: Sequence specific cleavage of DNA by Distamycin-EDTA—Fe(II) and EDTA-distamycin Fe(II)." *Tetrahedron*, 40(3):457-65 (1984).

Trauger, J.W. et al., "Recognition of DNA by designed ligands at subnanomolar concentrations." *Nature*, 382:559-61 (1996).

Vaquero et al., "Small ligands that neither bind to nor alter the structure of d(GA.TC)n sequences in DNA." *FEBS Letters*, 420:156-60 (1997).

Wade W.S. et al., "Binding affinities of synthetic peptides, pyridine-2-carboxamidonetropsin and 1-methylimidazole-2-carboxamidonetropsin, that form 2:1 complexes in the minor groove of double-helical DNA." *Biochemistry*, 32(42):11385-89 (1993).

Wade, W.S. et al., "Design of peptides that bind in the minor groove of DNA at 5'-(A,T)G(A,T)C(A,T)-3' sequences by a dimeric side-by-side motif." *J. Am. Chem. Soc.*, 114(23):8783-94 (1992).

Wade, W.S., "Sequence specific complexation of B DNA at sites containing G,C base pairs." Ph.D. Thesis, California Institute of Technology, Pasadena, CA (1989).

White, S. et al., "Recognition of the four Watson-Crick base pairs in the DNA minor groove by synthetic ligands." *Nature*, 391:468-71 (1998).

White, S. et al., "On the pairing rules for recognition in the minor groove of DNA by pyrrole-imidazole polyamides." *Chemistry & Biology*, 4:569-578 (1997).

Xie, G. et al., "Protein kinase C-α inhibitors; structure-activity relationships in bis-indole series." *Bioorg. Med. Chem. Lett.*, 5(5):497-500 (1995).

Xie, G. et al., Synthesis and DNA cleaving properties of hybrid molecules containing propargylic sulfones and minor groove binding lexitropsins. *Bioorg. Med. Chem. Lett.*, 3(8):1565-70 (1993).

Xue, C.B. et al, "Synthesis and Antiplatelet Effects of An Isoxazole Series of Glycoprotein IIb/IIIa Antagonists", *Bioorg. Med. Chem. Lett.*, 8:3499-3504 (1998).

Yamori, T. et al., "Potent antitumor activity of MS-247, a novel DNA minor groove binder, evaluated by an in vitro and in vivo human cancer cell line panel." *Cancer Res.*, 59(16):4042-49 (1999).

Zakrzewska, K. et al., "Drug recognition of DNA. Proposal for GC minor groove specific ligands: vinylexins." *J. Biomol. Struct. Dyn.*, 6(2):1043-1058 (1989).

Zakrzewska, K. et al., "Theoretical study of the sequence selectivity of isolexins, isohelical DNA groove binding ligands. Proposal for the GC minor groove specific compounds." *J. Biomol. Struct. Dyn.*, 5(5):1043-1058 (1988).

* cited by examiner

| Cpd | Y | $X^5$ | $X^6$ | $X^7$ | $X^8$ |
|-----|---|-------|-------|-------|-------|
| A-63 | O | H | H | H/Me | Me/H |
| A-77 | S | H | H | H | Me |
| A-78 | O | H | H | H/Et | Et/H |
| A-79 | O | H/Me | Me/H | Me/H | H/Me |
| A-80 | O | H/Me | Me/H | H/Me | Me/H |

ANTIBACTERIAL COMPOUNDS HAVING A (PYRROLE CARBOXAMIDE)-(BENZAMIDE)-(IMIDAZOLE CARBOXAMIDE) MOTIF

CROSS-REFERENCES TO RELATED APPLICATIONS

This application is a continuation of U.S. patent application Ser. No. 10/732,900, flied Dec. 9, 2003, which claims the benefit of U.S. Ser. No. 60/432,465, filed Dec. 10, 2002, the disclosures of which are incorporated herein by reference.

STATEMENT AS TO RIGHTS TO INVENTIONS MADE UNDER FEDERALLY SPONSORED RESEARCH OR DEVELOPMENT

This invention was made with Government support under Grant No. N65236-99-1-5427 awarded by the Space and Naval Warfare Systems Command. The Government has certain rights in this invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

1. Field of the Invention

This invention relates to aromatic compounds having antibacterial activity and methods for their synthesis and use.

2. Description of Related Art

The discovery of penicillin and other antimicrobials in the early and mid 20$^{th}$ century generated a period of optimism about the medical profession's ability to treat microbial infections. However, the evolution of drug-resistant microbe strains—with new ones being constantly discovered—has led to an appreciation of the continuing need to develop new antimicrobials, preferably ones that are structurally different from extant ones or Exemplary recent disclosures of new antibacterial compounds include Ge et al., WO 01/74898 (2001); Baird et al., U.S. application Ser. No. 10/132,887, filed Apr. 24, 2002; Bürli et al., U.S. application Ser. No. 10/165,856, filed Jun. 6, 2002; McMinn et al., U.S. application Ser. No. 10/165,433, filed Jun. 6, 2002; Bürli et al., U.S. application Ser. No. 10/165,857, filed Jun. 6, 2002; Bürli et al., U.S. application Ser. No. 10/165,764, filed Jun. 6, 2002; and Bürli et al., U.S. Provisional Application No. 60/400671, filed Aug. 2, 2002. The foregoing applications disclose antimicrobial compounds characterized by plural aromatic carboxamide units. The present invention relates to antimicrobial compounds also having plural aromatic carboxamide units, but with a distinguishable structural motif.

BRIEF SUMMARY OF THE INVENTION

The present invention provides compounds according to formula (I)

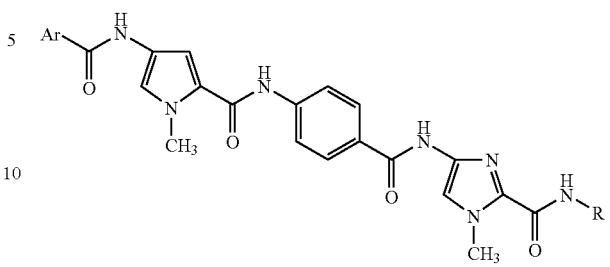

and the solvates, prodrugs, and pharmaceutically acceptable salts thereof, where Ar is an unsubstituted or substituted phenyl group, an unsubstituted or substituted 5-member heteroaryl group, an unsubstituted or substituted 6-member heteroaryl group, an unsubstituted or substituted 6,6-condensed ring aryl or heteroaryl group, an unsubstituted or substituted 5,5-condensed ring heteroaryl group; an unsubstituted or substituted 5,7-condensed ring aryl or heteroaryl group, or an unsubstituted or substituted 6,5-condensed ring heteroaryl group; and R is a $C_1$ to $C_{28}$ alkyl or heteroalkyl moiety containing a basic group having a $pK_b$ of 12 or less or a quaternized nitrogen group.

DETAILED DESCRIPTION OF THE INVENTION

Abbreviations and Definitions

Figure 1A:
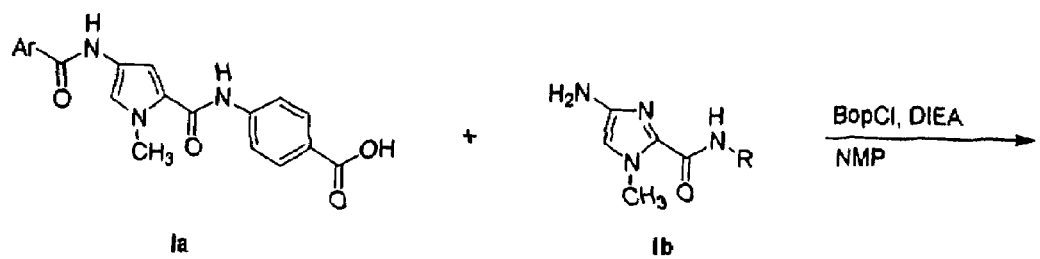
FIGS. 1a, 1b, and 2 through 13 show chemical reactions used to make compounds of this invention.
Figure 1A:
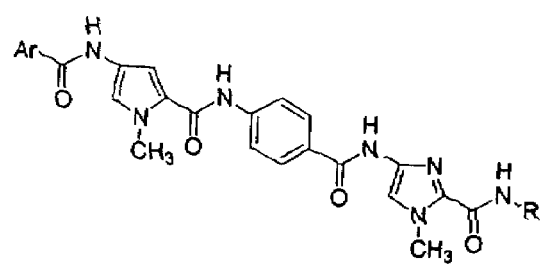

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having six or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydro-furan-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terns (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl, heteroalkyl, aryl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', 'N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2m'+1), where m' is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$) alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as halo-alkyl (e.g., —$CF_3$ and —$CH_2CF_3$) and acyl (e.g., —C(O)$CH_3$, —C(O)$CF_3$, —C(O)$CH_2OCH_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —S(O)$_2$R', —NH—C($NH_2$)=NH, —NR'C($NH_2$)=NH, —NH—C($NH_2$)=NR', —S(O)R', —S(O)$_2$NR'R", —$N_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—($CH_2$)$_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-($CH_2$)$_r$—B—, wherein A and B are independently —CH₂—, —O—, —NH—, —S—, —S(O)—, —S(O)₂—, —S(O)₂NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH₂)ₛ—X—(CH₂)ₜ—, where s and t are independently integers of from 0 to 3, and X is —O—, —NR'—, —S—, —S(O)—, —S(O)₂—, or —S(O)₂NR'—. The substituent R' in —NR'— and —S(O)₂NR'— is selected from hydrogen or unsubstituted (C₁-C₆)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, ascorbic, propionic, isobutyric, maleic, malonic, lactic, malic, glutamic, benzoic, succinic, suberic, fumaric, mandelic, phthalic, benzenesulfonic, p-tolylsulfonic, citric, tartaric, methanesulfonic, lactobionic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (chiral centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium (³H), iodine-125 (¹²⁵I) or carbon-14 (¹⁴C). All isotopic variations of the compounds of the present invention, whether radioactive or not, are intended to be encompassed within the scope of the present invention.

Compounds

Compounds of this invention have, as a characteristic structural motif, the sequence an N-methylpyrrole carboxamide unit ("Py'"), ap-benzamide unit ("Ph"), and a 1-methylimidazole carboxamide unit ("Im"), as shown following:

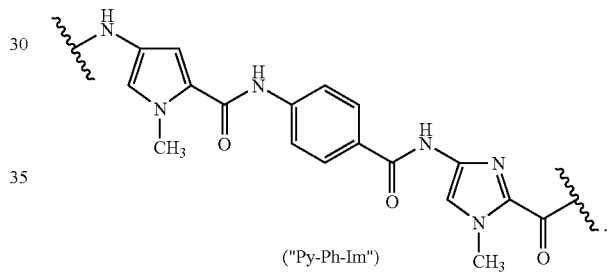

("Py-Ph-Im")

The Py-Ph-Im motif is embodied in compounds (I)

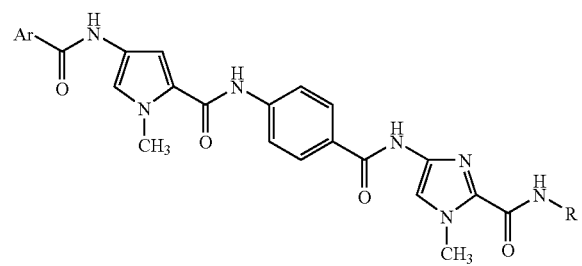

(I)

and the solvates, prodrugs, and pharmaceutically acceptable salts thereof, where Ar is an unsubstituted or substituted phenyl group, an unsubstituted or substituted 5-member heteroaryl group, an unsubstituted or substituted 6-member heteroaryl group, an unsubstituted or substituted 6,6-condensed ring aryl or heteroaryl group, an unsubstituted or substituted 5,5-condensed ring heteroaryl group; an unsubstituted or substituted 5,7-condensed ring aryl or heteroaryl group, or an unsubstituted or substituted 6,5-condensed ring heteroaryl group; and R is a $C_1$ to $C_{28}$ (preferably $C_1$ to $C_{18}$) alkyl or heteroalkyl moiety containing a basic group having a $pK_b$ of 12 or less or a quaternized nitrogen group.

Exemplary 5-member heteroaryl groups include imidazolyl, pyrrolyl, pyrazolyl, furanyl, isothiazolyl, oxazolyl, isoxazolyl, thiazolyl, furazanyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,3,4-oxadiazolyl, 1,2,4-oxadiazolyl, and thienyl groups. Exemplary 6-member heteroaryl groups include pyridyl, pyrimidyl, pyrazinyl, pyridazinyl, and triazinyl groups. Exemplary 6,6-condensed ring aryl or heteroaryl groups include naphthyl, quinolyl, and isoquinolyl groups. Exemplary 6,5-condensed ring heteroaryl groups include benzothienyl, indolyl, and benzofuranyl groups.

Preferably, the moiety Ar is selected from the group consisting of

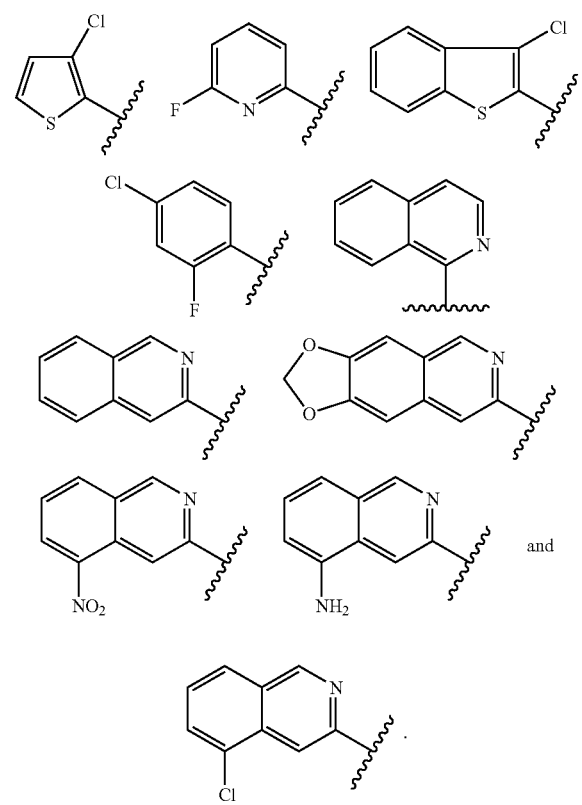

The moiety R preferably is

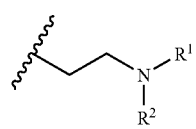

where $R^1$ and $R^2$ independently are $C_1$ to $C_{16}$ alkyl or heteroalkyl moieties and may join together to form, together with the nitrogen to which they are bound, a 5 to 7 member ring. Either $R^1$ or $R^2$, or both, may be substituted or unsubstituted.

Examples of preferred moieties R include:

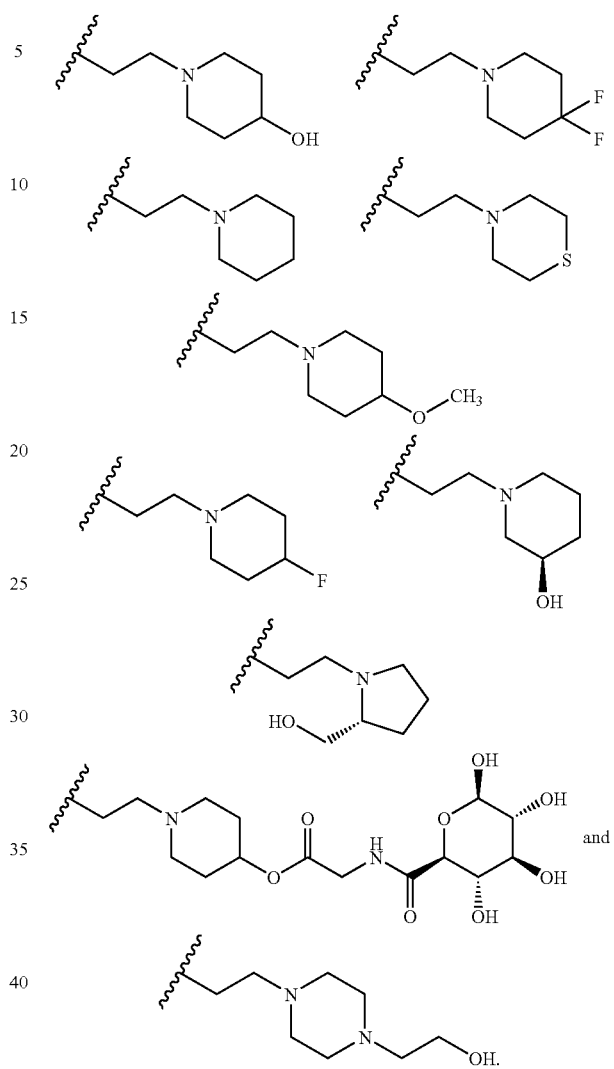

The R moiety in compound (I) has a basic group having a $pK_b$ of 12 or less or a quaternized nitrogen group. (Or, stated conversely, the conjugate acid of the basic group has a $pK_a$ greater than 2 ($pK_a=14-pK_b$).) Preferably, the $pK_b$ is less than 10, more preferably less than 5. Preferably the basic group is a nitrogenous group, for example an amine, an amidine, a guanidine, a pyridine, a pyridazine, a pyrazine, a pyrimidine, an imidazole, or an aniline. Primary, secondary, or tertiary aliphatic amines are preferred, such as:

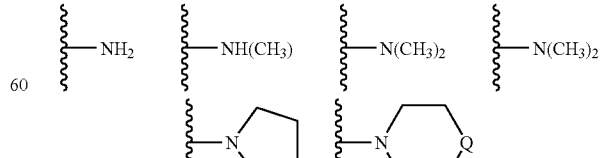

(Q = $CH_2$, O, S, NH, CH(OH), C($F_2$), N($CH_3$), CHF, CH($CO_2H$), CH($OCH_3$))

and the like. Exemplary quaternized nitrogen groups include alkyl pyridinium and tetraalkyl ammonium groups such as:

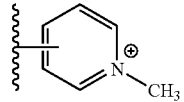 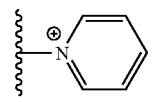 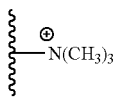

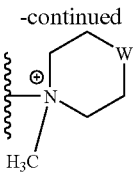

(W = CH$_2$, O, S)

Specific examples of compounds (I) are shown in Table A.

TABLE A

Compounds (I)

| Ref. | Ar | R |
|---|---|---|
| A-1 | 3-chloro-thiophen-2-yl | 3-(4-hydroxypiperidin-1-yl)propyl |
| A-2 | 6-fluoro-pyridin-2-yl | 3-(4-hydroxypiperidin-1-yl)propyl |
| A-3 | 3-chloro-benzo[b]thiophen-2-yl | 3-(4-hydroxypiperidin-1-yl)propyl |
| A-4 | 4-chloro-2-fluoro-phenyl | 3-(4-hydroxypiperidin-1-yl)propyl |
| A-5 | isoquinolin-1-yl | 3-(4-hydroxypiperidin-1-yl)propyl |
| A-6 | [1,3]dioxolo[4,5-g]isoquinolin-6-yl | 3-(4-hydroxypiperidin-1-yl)propyl |
| A-7 | 5-nitro-isoquinolin-3-yl | 3-(4-hydroxypiperidin-1-yl)propyl |

TABLE A-continued
Compounds (I)
| Ref. | Ar | R |
|---|---|---|
| A-8 | 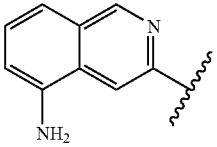 | 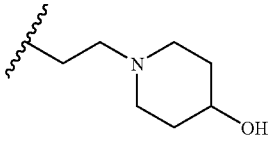 |
| A-9 | 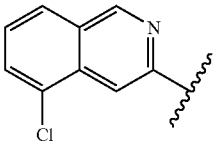 | 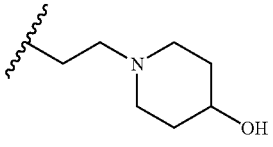 |
| A-10 | 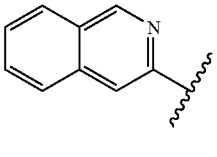 | 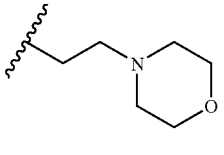 |
| A-11 | 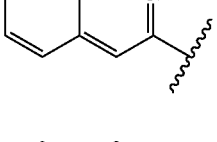 | 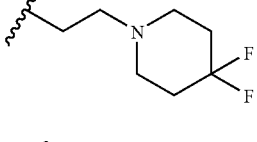 |
| A-12 | 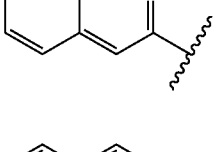 | 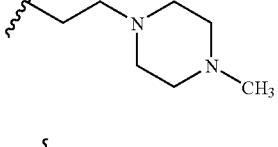 |
| A-13 | 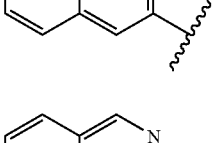 | 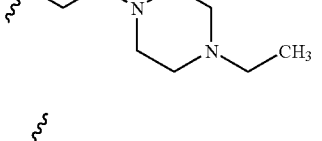 |
| A-14 | 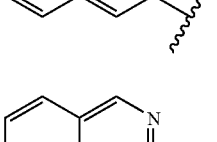 | 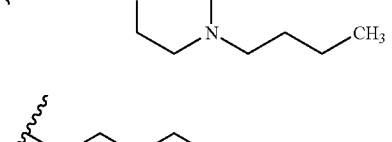 |
| A-15 | 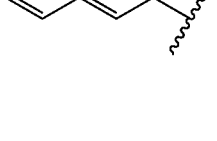 | 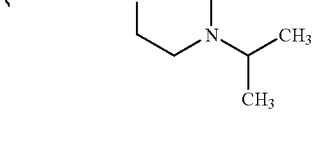 |
| A-16 | 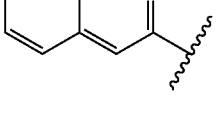 | 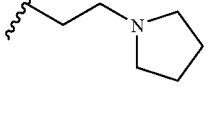 |

TABLE A-continued
Compounds (I)
| Ref. | Ar | R |
|---|---|---|
| A-17 | 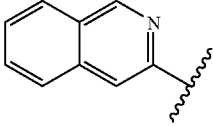 | 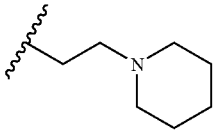 |
| A-18 | 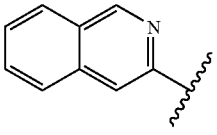 | 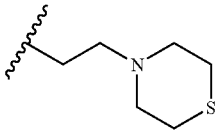 |
| A-19 | 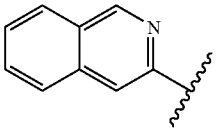 | 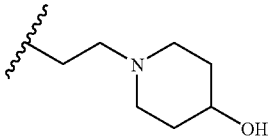 |
| A-20 | 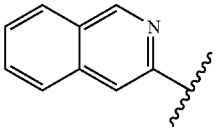 | 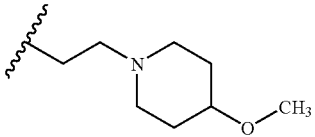 |
| A-21 | 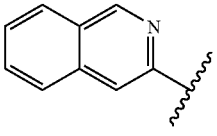 | 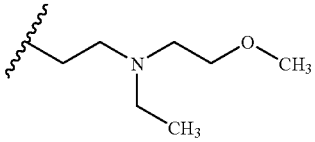 |
| A-22 | 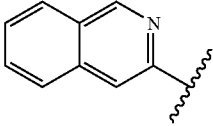 | 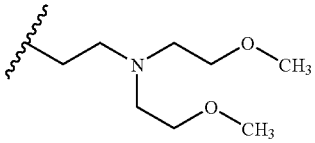 |
| A-23 | 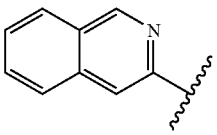 | 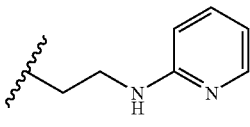 |
| A-24 | 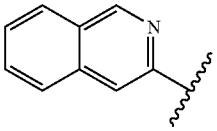 | 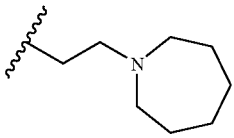 |
| A-25 | 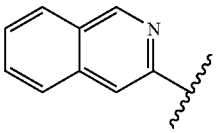 | 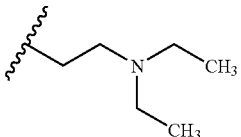 |
| A-26 | 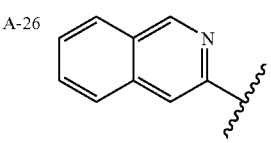 | 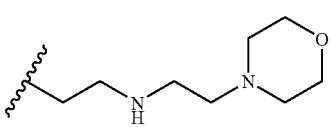 |

TABLE A-continued
Compounds (I)
| Ref. | Ar | R |
|---|---|---|
| A-27 | 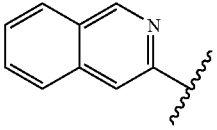 | 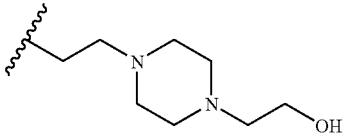 |
| A-28 | 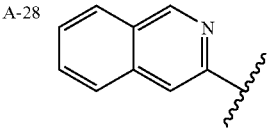 | 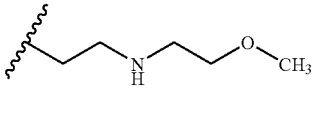 |
| A-29 | 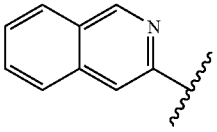 | 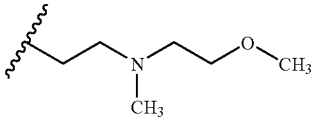 |
| A-30 | 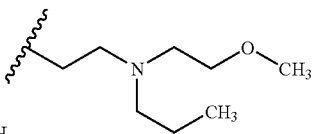 | 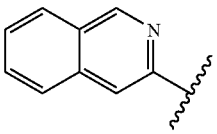 |
| A-31 | 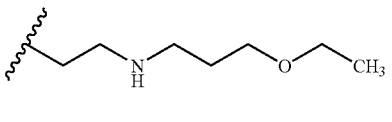 | 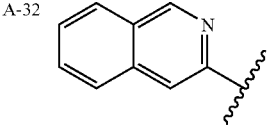 |
| A-32 | 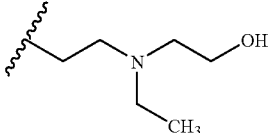 | 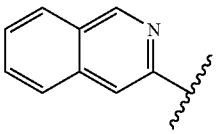 |
| A-33 | 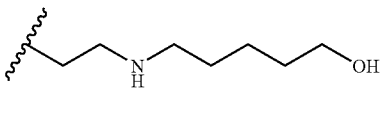 | 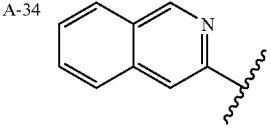 |
| A-34 | 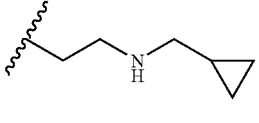 | 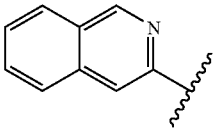 |
| A-35 | 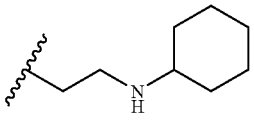 | 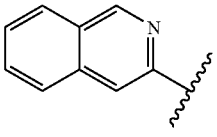 |
| A-36 | 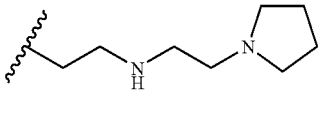 | |

TABLE A-continued
Compounds (I)
| Ref. | Ar | R |
|---|---|---|
| A-37 | 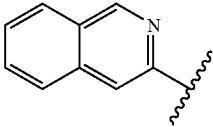 | 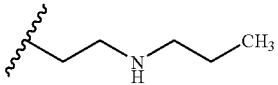 |
| A-38 | 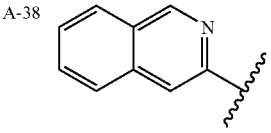 | 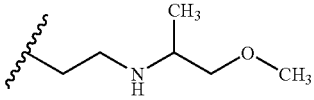 |
| A-39 | 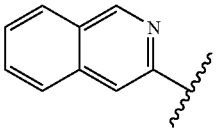 | 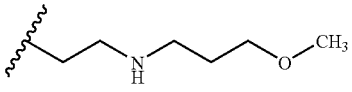 |
| A-40 | 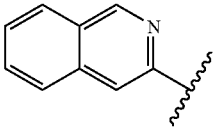 | 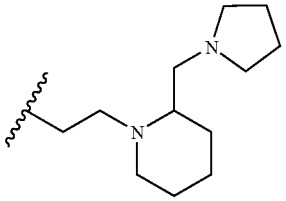 |
| A-41 | 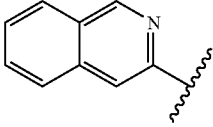 | 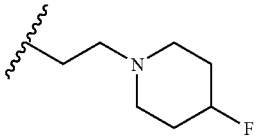 |
| A-42 | 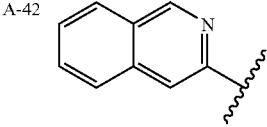 | 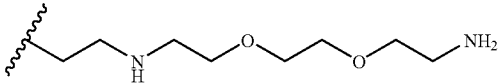 |
| A-43 | 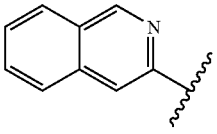 | 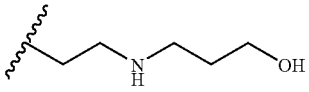 |
| A-44 | 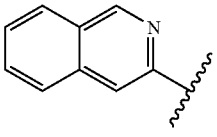 | 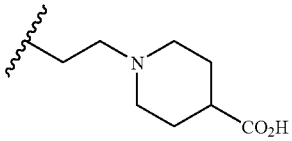 |
| A-45 | 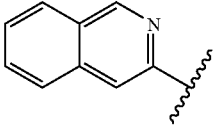 | 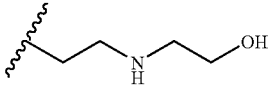 |

TABLE A-continued
Compounds (I)
| Ref. | Ar | R |
|---|---|---|
| A-46 |  | 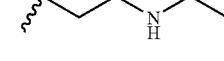 |
| A-47 |  | 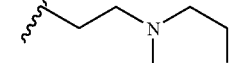 |
| A-48 |  | 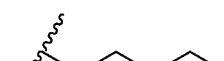 |
| A-49 |  |  |
| A-50 |  | 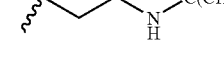 |
| A-51 |  | 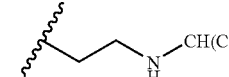 |
| A-52 |  |  |
| A-53 |  |  |
| A-54 |  |  |

TABLE A-continued
Compounds (I)
| Ref. | Ar | R |
|---|---|---|
| A-55 | 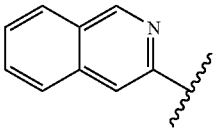 | 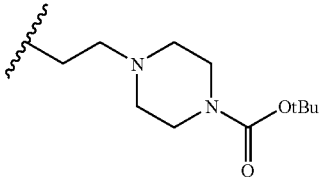 |
| A-56 | 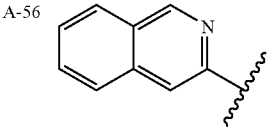 | 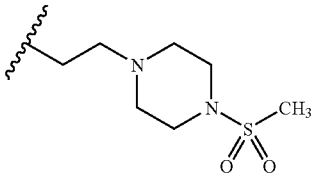 |
| A-57 | 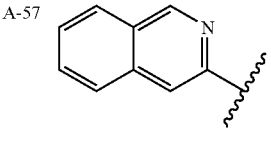 | 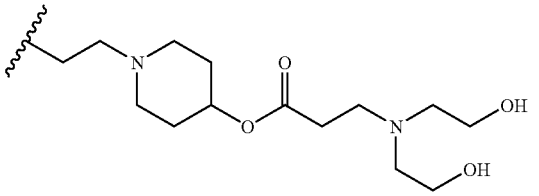 |
| A-58 | 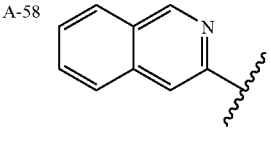 | 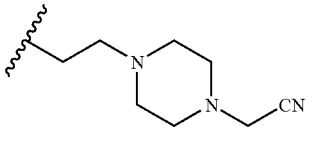 |
| A-59 | 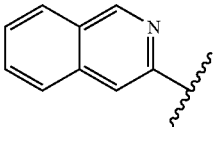 | 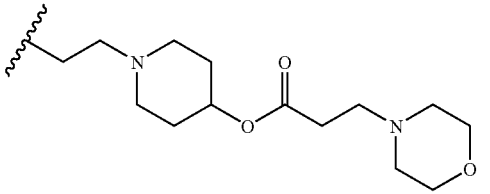 |
| A-60 | 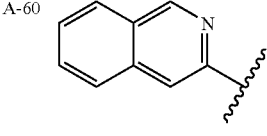 | 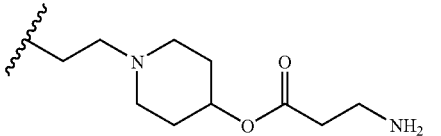 |
| A-61 | 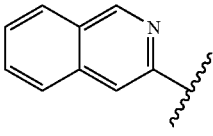 | 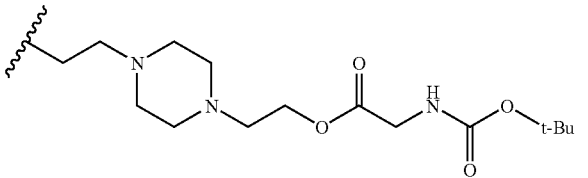 |
| A-62 | 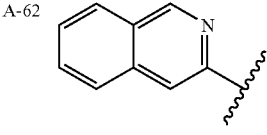 | 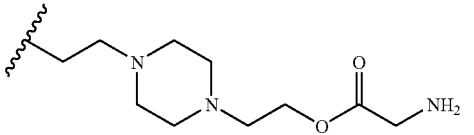 |

TABLE A-continued
Compounds (I)
| Ref. | Ar | R |
|---|---|---|
| A-63 | 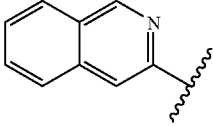 |  |
| A-64 | 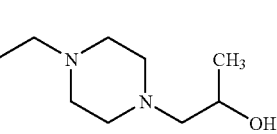 | 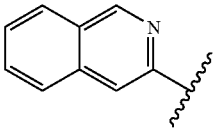 |
| A-65 |  | 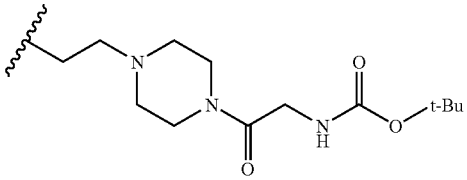 |
| A-66 | 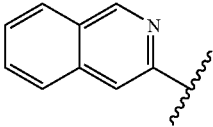 |  |
| A-67 | 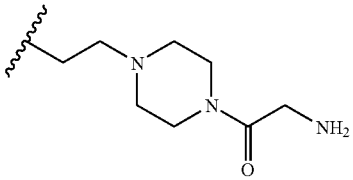 | 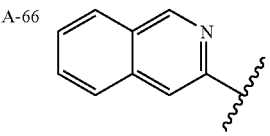 |
| A-68 |  | 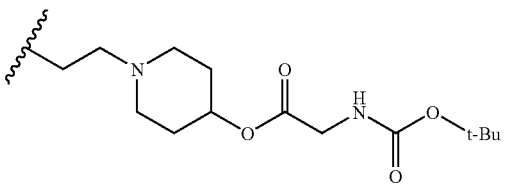 |
| A-69 | 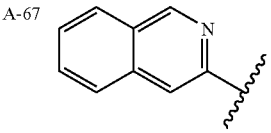 |  |
| A-70 | 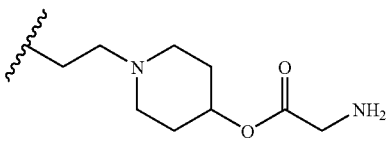 | 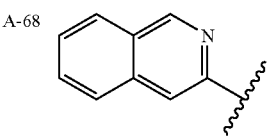 |
| A-71 |  | 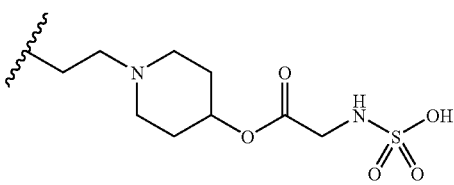 |

TABLE A-continued
Compounds (I)
| Ref. | Ar | R |
|---|---|---|
| A-72 | 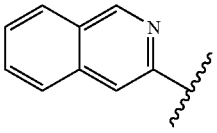 | 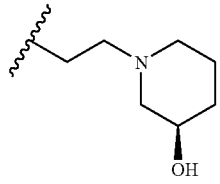 |
| A-73 | 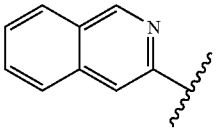 | 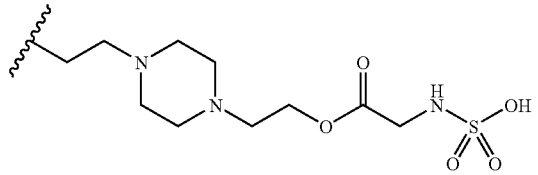 |
| A-74 |  | 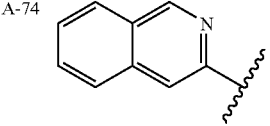 |
| A-75 | 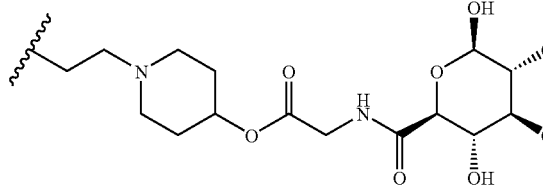 |  |
| A-76 | 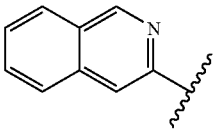 | 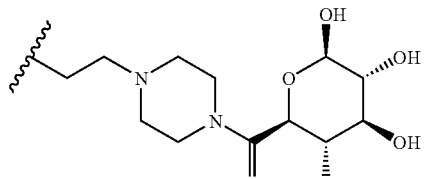 |
| A-77 |  | 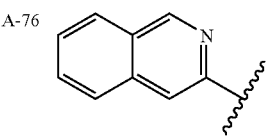 |
| A-78 | 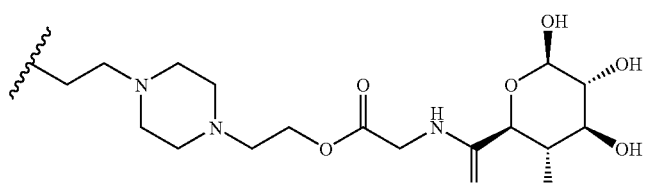 |  |
| A-79 | 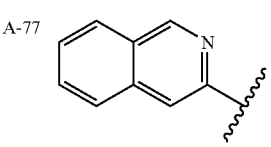 | 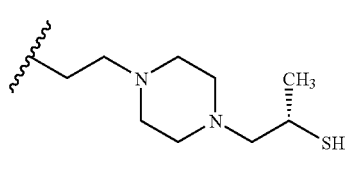 |

TABLE A-continued

Compounds (I)

| Ref. | Ar | R |
|---|---|---|
| A-80 | 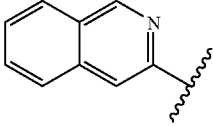 | 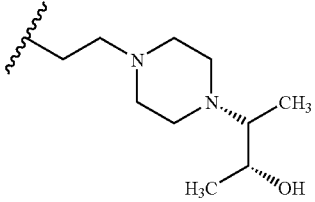 |
| A-81 | 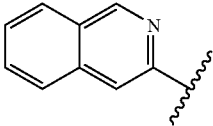 | 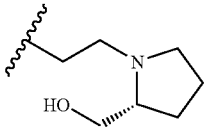 |

Those skilled in the art will appreciate that some of the compounds in Table (I) are prodrugs, which are convertible to active compounds (I). Examples of prodrug compounds (I) include compounds A-59 to A-62, A-66 to A-67, and A-73 to A-74. They will also appreciate that some compounds (I) in Table A can serve as intermediates for the synthesis of other compounds (I) (e.g., compound A47 and A-62).

Compounds of this invention have been found to have anti-bacterial and/or antifungal properties and therefore may be used for preventing and/or treating infections in eukaryotic organisms. For human anti-infective applications, an effective amount of a compound of this invention is used, optionally in combination with a pharmaceutically acceptable carrier. The composition may be dry, or it may be a solution. Treatment may be reactive, for combating an existing infection, or prophylactic, for preventing infection in an organism susceptible to infection. Preferably, compounds of this invention are used to treat infections by drug-resistant strains of bacteria, for example MRSA (methicillin resistant *S. aureus*), MRSE (methicillin resistant *S. epidermidis*), PRSP (penicillin resistant *S. pneumoniae*) or VRE (vancomycin resistant *Enterococci*). By "drug-resistant" it is meant that the bacteria are resistant to treatment with conventional antibiotics.

Host organisms that can be treated include eukaryotic organisms, in particular plants and animals. The plant may be an agriculturally important crop, such as wheat, rice, corn, soybean, sorghum, and alfalfa. Animals of interest include mammals such as bovines, canines, equines, felines, ovines, porcines, and primates (including humans). Thusly, in another aspect of this invention, there is provided a method for treating a bacterial infection—particularly an infection by Gram-positive bacteria—comprising administering to a patient in need of such treatment an effective amount of compound (I). Compounds of this invention can be used in the preparation of a medicament for treating a bacterial or fungal infection in a mammal. The compounds may be administered orally, topically, parenterally (e.g., intravenously, subcutaneously, intraperitoneally, transdermally) or by inhalation.

The practice of our invention can be further understood by reference to the following examples, which are provided by way of illustration and not of limitation.

Synthesis—General Remarks

Common abbreviations and acronyms are employed for various terms, including: Boc for t-butyloxycarbonyl (and (Boc)$_2$O for the corresponding anhydride); BopCl for bis(2-oxo-3-oxazolidinyl)phosphinic chloride; DIEA for diisopropylethylamine; DCC for dicyclohexylcarbodiimide; DMAP for 4-(dimethylamino)pyridine; DMF for N,N-dimethyl-formamide; HATU for O-(7-azabenzotriazol-1-yl)-N,N,N',N'-tetramethyluronium hexa-fluorophosphate; HBTU for 2-(1H-benzotriazole-1-yl)-1,1,3,3-tetramethyluronium hexa-fluorophosphate; MP-CNBH$_3$ for MP-cyanoborohydride; NMP for N-methylpyrrolidone; Et$_2$O for diethyl ether; AcOEt for ethyl acetate; PyBop for benzotriazole-1-yl-oxytripyrrolidinophosphonium hexafluorophosphate; RT for room (ambient) temperature; and $^1$H-NMR for proton NMR.

The structures of intermediate and final compounds were confirmed by $^1$H-NMR and mass spectrometry. Unless noted otherwise, the $^1$H-NMR and mass spectra were consistent with the assigned structures and did not indicate the presence of significant impurities.

The skilled artisan will understand that: (a) an intermediate described in the context of the synthesis of a particular compound of this invention can also be used to make other compounds of this invention, *mutatis mutandis*; (b) in certain experimental sections only the preparation of an intermediate compound is described, because its incorporation into a final compound of this invention straightforwardly follows synthetic methodology described herein; and (c) for some reactions that recur herein, detailed reaction and work-up conditions sometimes are not provided in each instance in the interest of brevity and that the conditions described elsewhere in this application are adaptable to the instance at hand without undue experimentation.

Synthesis—General Procedures

Figure 1B:
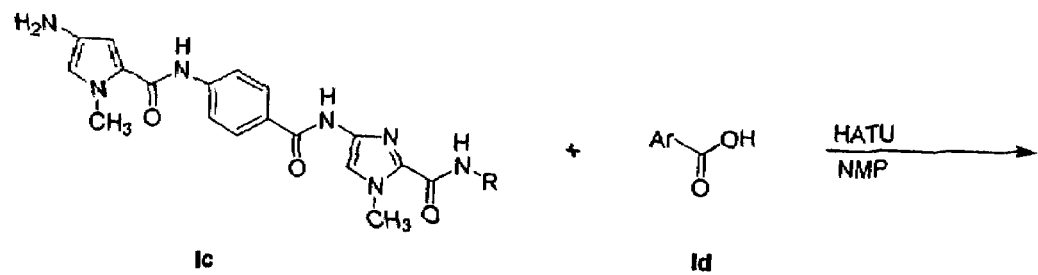
Figure 1B:
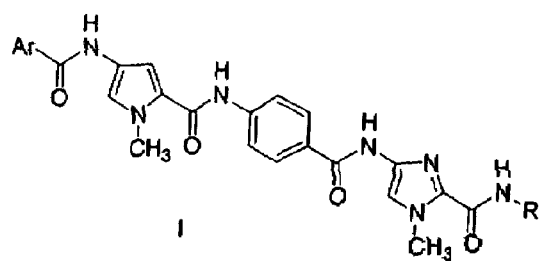

Two general synthetic strategies for making compounds (I) are described. In FIG. 1a, intermediate (Ia) containing Ar, Py, and Ph is coupled with a complementary intermediate (Ib) containing Im and R (or a precursor of R) to yield a compound (I). In FIG. 1b, intermediate (Ic) containing Py, Ph, Im and R (or a precursor of R) is coupled with an aromatic carboxylic acid (Id) to yield a compound (I). In either scheme, the R group can be further modified or derivatized after the coupling step to yield a different desired R in a compound (I). Generally, final compounds were purified using reverse phase HPLC (Hamilton PRP-1 column, CH$_3$CN/0.5% aqueous AcOH, 0% to 60% in 60 min, UV detection at 310 nm).

Synthesis—Specific Compounds

EXAMPLE A

Figure 2:
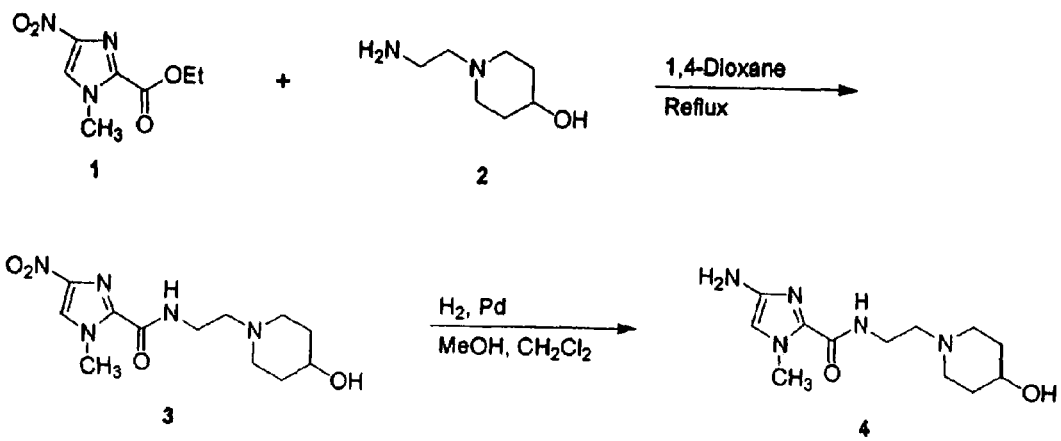

Amine 4. Referring to FIG. 2, a solution of ethyl 1-methyl-4-nitroimidazole-2-carboxylate 1 (10.0 g, 50 mmol) and 1(2-aminoethyl)-4-hydroxypiperidine 2 (10.0 g, 69 mmol) in 1,4-dioxane (10 mL) was refluxed for 1 h, cooled to RT and treated with $CH_2Cl_2$ (200 mL). The organic solution was washed with $H_2O$ (3×100 mL) and brine (50 mL) and dried ($Na_2SO_4$). The solvent was evaporated and the resulting solid was recrystallized from AcOEt/hexane twice to give yellow crystalline nitro compound 3 (5 g, 34% yield). Nitro compound 3 (3.0 g, 10 mmol) was dissolved in $CH_2Cl_2$/MeOH (100 ml; 10:1) and treated with Pd/carbon black (150 mg). The mixture was stirred under $H_2$ atmosphere (5 atm) at RT for 2 h and filtered through Celite. Evaporation of the filtrate gave the amine 4 (2.5 g, 93%), which was used in subsequent coupling reactions without further purification.

EXAMPLE B

Figure 3:
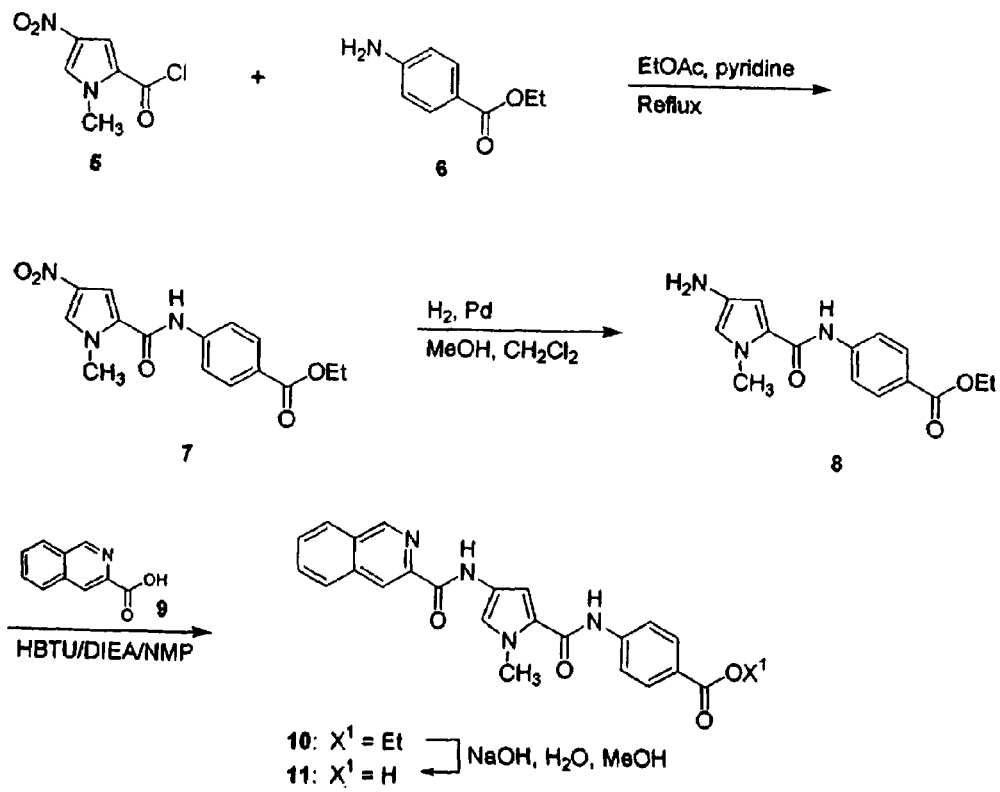

Carboxylic Acid 11. Referring to FIG. 3, a solution of amino ester 6 (2.7 g) in AcOEt (20 mL) was treated with pyridine (20 mL) and nitro acid chloride 5 (3.6 g) at RT, refluxed for 1 h, cooled to RT, and diluted with AcOEt (200 mL) and $H_2O$ (100 mL). The organic layer was washed with $H_2O$ (3×100 mL) and brine. Evaporation of the solvent gave nitro ester 7 as a yellow solid. Pd-catalyzed hydrogenation (similarly to above) of nitro ester 7 in MeOH gave the amino ester 8.

A solution of isoquinoline carboxylic acid 9 (1.5 g), HBTU (3.7 g), and DIEA (2 mL) in NMP (30 mL) was stirred at 35° C. for 30 min, treated with amino ester 8 (2.2 g), and stirred for 2 h at 60° C. After cooling to RT, the mixture was poured into ice-water (300 mL) and the resulting precipitate was washed with $H_2O$ (3×50 mL) and dried to yield trimeric ester 10. Treatment of the ester 10 with 1M NaOH in MeOH/$H_2O$ at 60° C. for 2 h, and acidification with 1M HCl to pH 5 caused formation of a precipitate, which was washed with $H_2O$ and dried to yield carboxylic acid 11 as a pale solid.

EXAMPLE C

Figure 4:
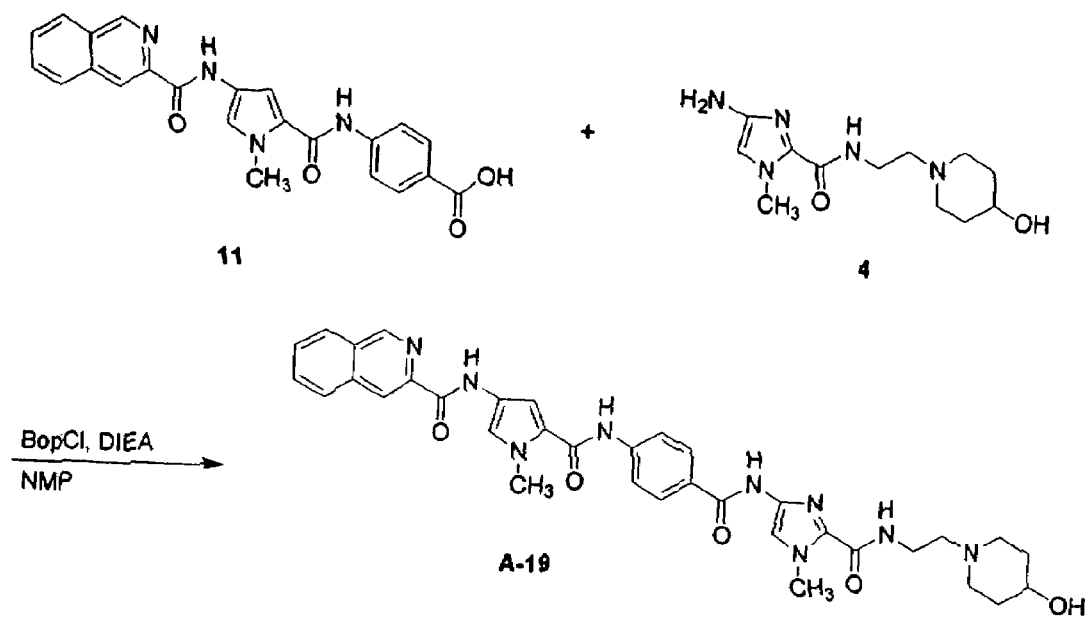

Compound A-19. Referring to FIG. 4, a solution of carboxylic acid 11 (5.0 g, 12.0 mmol) and BopCl (3.0 g, 13.2 mmol) in NMP (40 mL) was treated at RT with DIEA (3.1 g, 24.0 mmol) and DMAP (0.3 g, 2.5 mmol), stirred for 30 min, and treated with a solution of amine 4 (3.5 g, 13.3 mmol) in NMP (5 mL). The mixture was stirred at 60° C. for 30 min and poured into 450 mL stirring ice-water. The resulting precipitate was collected, washed with $H_2O$ (2×100 mL), and lyophilized to give compound A-19 (4.1 g, 52% yield). $^1$H-NMR (300 MHz, d6-DMSO) δ 10.90 (s, 1H), 10.70 (s, 1H), 10.17 (s, 1H), 9.46 (s, 1H), 8.65 (s, 1H), 8.28 (d, J=6.0 Hz, 1H), 8.26 (d, J=6.0 Hz, 1H), 7.99 (d, J=6.3 Hz, 2H), 7.95~7.75 (comp, 5H), 7.59 (s, 1H), 7.53 (s, 1H), 7.45 (s, 1H), 4.54 (s, 1H), 3.95 (s, 3H), 3.89 (s, 3H), 3.42 (m, 2H), 2.72 (m, 2H), 2.42 (m, 2H), 2.04 (m, 2H), 1.69 (m, 2H), 1.38 (m, 2H).

Examples A, B, and C in combination illustrate the synthesis of a compound (I) using the general approach of FIG. 1a with specific reference to compound A-19, but other compounds (I) can be made in like manner by using analogs of carboxylic acid 11 and/or amine 4 to yield such other compounds (I). Compound A-10 was synthesized by such a method.

EXAMPLE D

Figure 5:
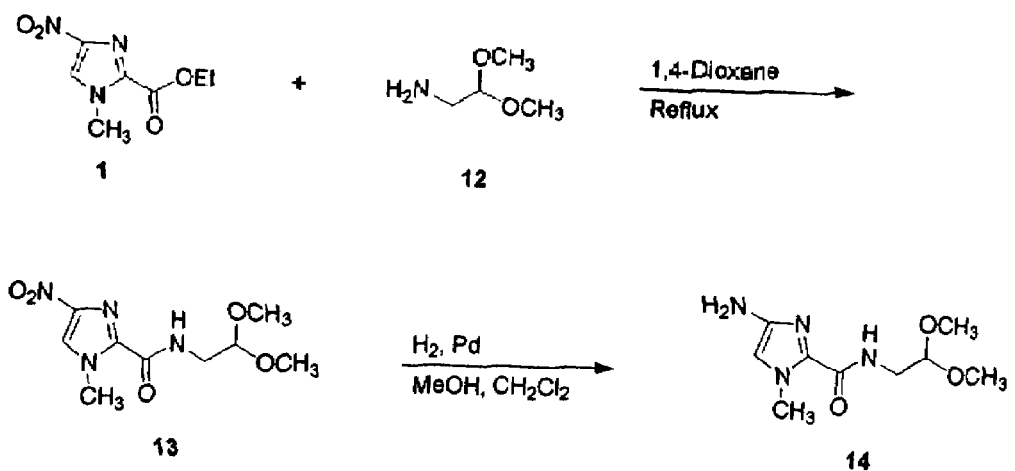

Amine-acetal 14. Referring to FIG. 5, a mixture of ethyl 1-methyl-4-nitroimidazole-2-carboxylate 1 (4.0 g, 20 mmol) and 2,2-dimethoxyethylamine 12 (3.5 g, 33 mmol) was stirred at 110° C. for 20 min, treated with AcOEt (200 mL) and washed with $H_2O$ (3×50 mL) and brine, and dried ($Na_2SO_4$). The solution was concentrated to 20 mL, treated with hexanes (100 mL), and cooled to –10° C. for 12 h to yield yellow crystals of nitro-acetal 13 (3.5 g, 69% yield). Hydrogenation of nitro-acetal 13 was conducted according the same procedure described for amine 4 above to give the acetal 14 quantitatively.

EXAMPLE E

Figure 6:
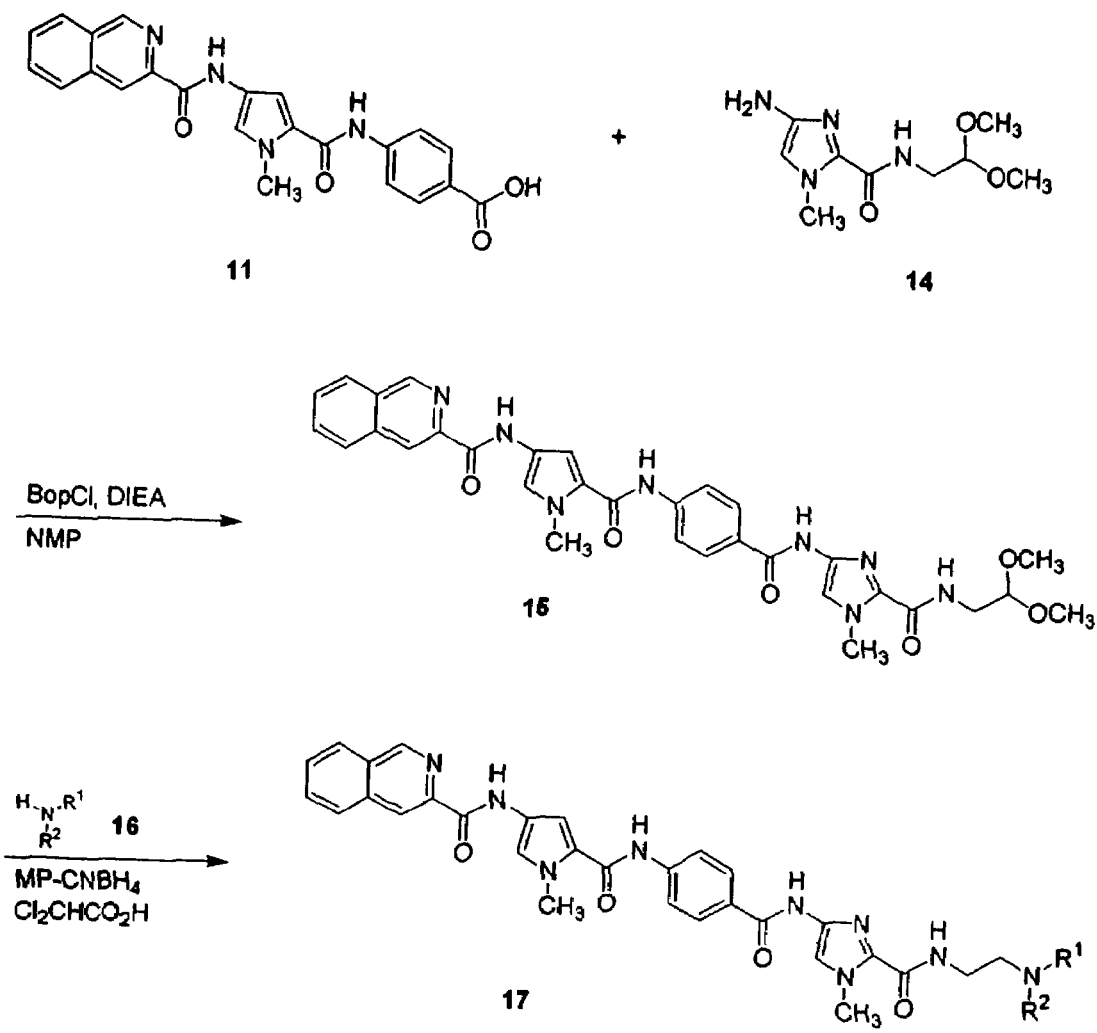

Compound 15. Referring to FIG. 6, a solution of carboxylic acid 11 (4.6 g, 11.1 mmol) and BopCl (2.81 g, 11.1 mmol) in NMP (30 mL) was treated with DIEA (7.0 mL) and DMAP (0.12 g, 1.1 mmol), stirred at RT for 30 min, treated with a solution of the acetal 14 (3.2 g, 14.0 mmol) in NMP (3 mL), and stirred at 60° C. for 30 min. The solution was poured into 300 mL stirring ice-water. The resulting precipitate was collected by filtration and washed with $H_2O$ (2×50 mL), dried under lyophilizing to give compound 15 (5.2 g, 75% yield). Compound 15, bearing the Ar-Py-Ph-Im scaffold, is a versatile intermediate for the synthesis of compounds (I), as illustrated in Example F, following.

EXAMPLE F

Compound 17. Still referring to FIG. 6, MP-cyanoborohydride (200 mg) was added to a solution of compound 15 (70 mg) and amine 16 (100 mg) in THF (3 mL). $Cl_2CHCO_2H$ (0.5 mL) was added. The mixture was sealed and put in a microwave reactor for 10 min at 150° C. The solids were removed by filtration and the resulting solution purified by HPLC to give compound 17.

Examples D, E and F in combination illustrate a variant of the approach of FIG. 1a by which numerous compounds (I) can be made by the reductive amination of compound 15 using a desired amine 16. Specific examples of compounds made in this manner include: A-11 to A-18, A-20 to A-46, A-48 to A-52, A-54, A-69 to A-72, and A-81.

EXAMPLE G

Figure 7:
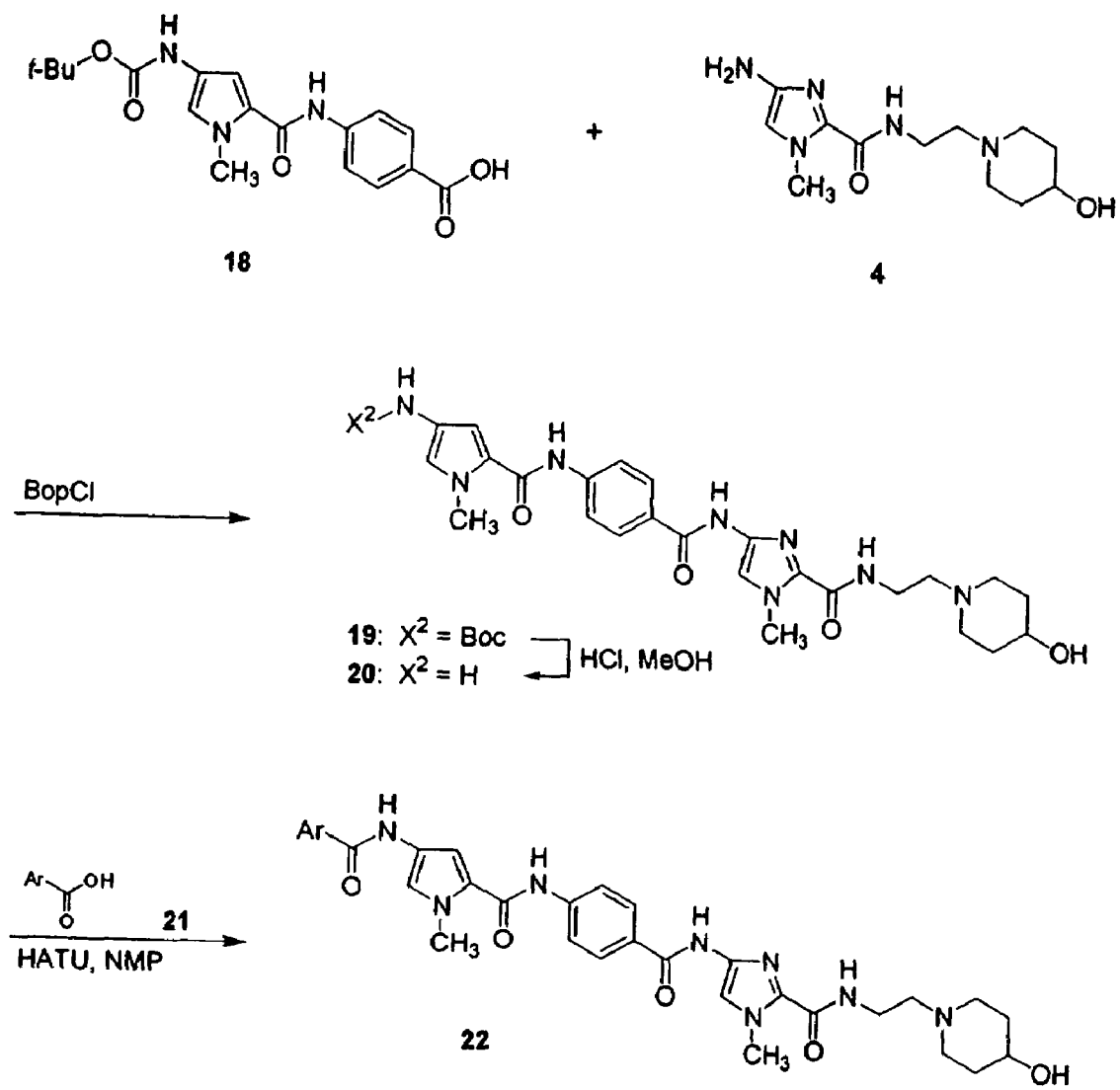

Compound 18. Referring to FIG. 7, the dimer 18 was prepared by coupling the Boc-protected amino-pyrrole OBt ester to ethyl 4-amino benzoate in DMF at 90° C. for 15 hours.

Compound 20. Still referring to FIG. 7, a solution of carboxylic acid 18 (1.7 g, 4.5 mmol) and BopCl (1.27 g, 5.0 mmol) in NMP (20 mL) was treated with DIEA (1.3 g, 10.0 mmol) and DMAP (0.12 g, 1.0 mmol), stirred at RT for 30 min, treated with a solution of amine 4 (1.34 g, 5.0 mmol) in NMP (2 mL), and stirred at 60° C. for 30 min. The solution was poured into 300 mL stirring ice-water. The resulting precipitate was collected by filtration, washed with $H_2O$ (2×100 mL), and lyophilized to give protected compound 19 (1.46 g, 54% yield). A solution of 19 (0.80 g) in MeOH (10 mL) was treated at RT with HCl gas, stirred for 30 min, and treated with $Et_2O$ (100 mL). The resulting precipitate was collected by filtration and dried to give the amine 20 as the hydrochloride salt (700 mg, 92%).

EXAMPLE H

Compound 22. Still referring to FIG. 7, a mixture of carboxylic acid 21 ($ArCO_2H$, 0.12 mmol, 1.2 eq), HATU (46 mg, 0.12 mol), DIEA (31 mg, 0.24 mmol) in NMP (1 mL) was stirred at RT for 30 min, treated with a solution of amine 20 (58 mg, 0.1 mmol, HCl salt) in DIEA (65 mg, 0.5 mmol) and NMP (1 mL), and stirred at 60° C. for 30 min. Preparative HPLC purification of the crude material gave compound 22.

Examples F and G in combination illustrate the synthesis of compounds (I) by the general approach of FIG. 1b. A variety of compounds (I) can be synthesized by the selection of an appropriate carboxylic acid 21 for coupling with amine 20. Examples of compounds synthesized in this manner include compounds A-1 to A-7 and A-9.

EXAMPLE I

Figure 8:
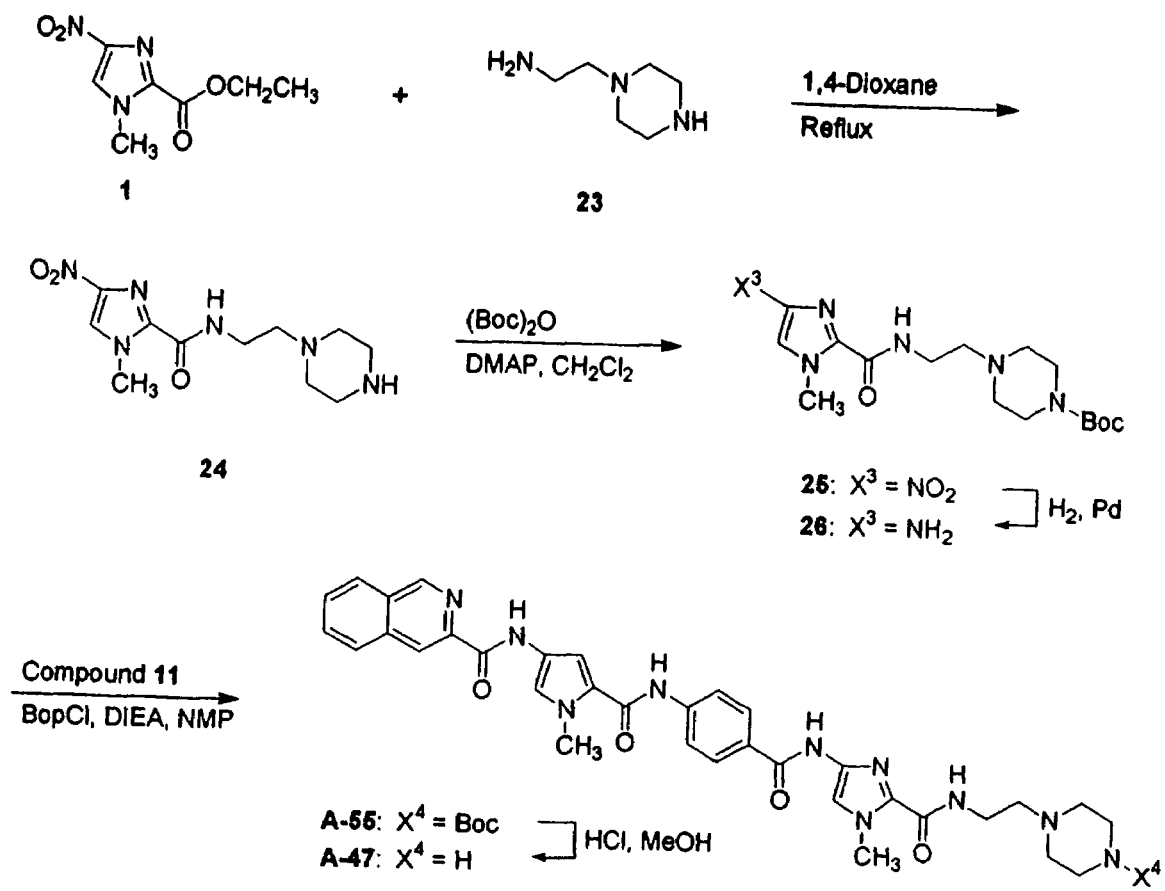

Compound A-47. Referring to FIG. 8, mixture of ethyl ester 1 (20 g) and 1(2-aminoethyl)piperazine 23 (20 g) was heated to 100° C. for 10 min in dioxane. After cooling to RT, $Et_2O$ (1000 mL) was added to the mixture. The resulting precipitate was collected by filtration and washed with AcOEt (3×200 mL), $Et_2O$ (2×100 mL) and dried to give nitro intermediate 24 (23 g, 82% yield). A solution of nitro intermediate 24 (5.6 g) in $CH_2Cl_2$ (100 mL) was treated at RT with $(Boc)_2O$ (4.8 g) and DMAP (0.24 g), stirred for 1 hour, and washed with 0.1 N NaOH (50 mL), $H_2O$ (50 mL) and brine, and dried ($Na_2SO_4$). Evaporation of the solvent left nitro compound 25 as a yellow solid (4.5 g, 52% yield). Pd-catalyzed hydrogenation of nitro compound 25 in MeOH and $CH_2Cl_2$ yielded the corresponding amino imidazole 26 quantitatively. Coupling of amino imidazole 26 with carboxylic acid 11 was conducted using the procedure of Example C to give compound A-55. Deprotection of compound A-55 with HCl in MeOH (as above) afforded compound A-47 as the hydrochloride salt.

EXAMPLE J

Figure 9:
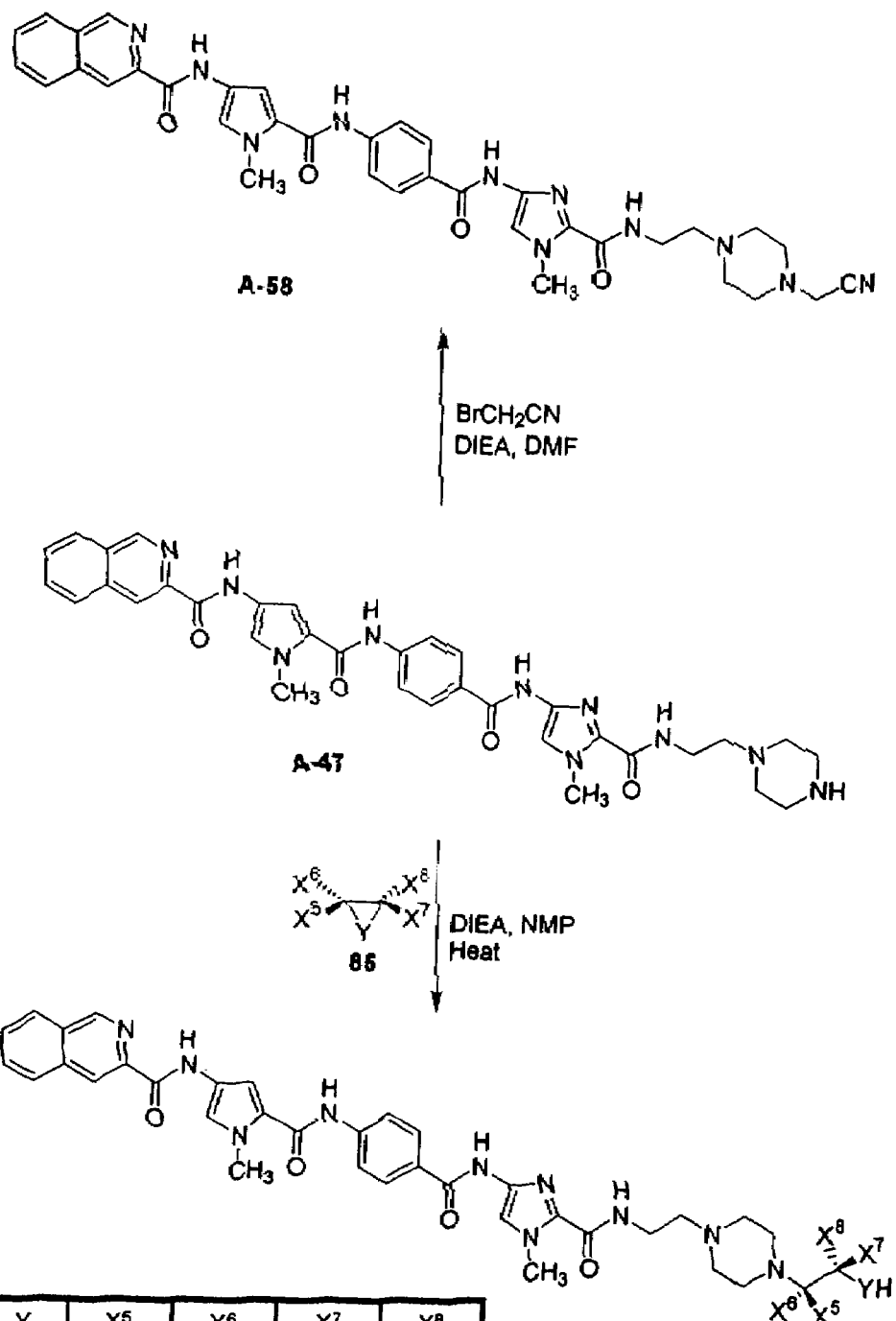

Compound A-63. FIG. 9 illustrates the synthesis of compound A-63 and its cognate compounds A-77 to A-80. The procedure is described here with specific reference to compound A-63: A solution of compound A-47 hydrochloride (115 mg) and propylene oxide (200 mg) in NMP (1 mL) and DIEA (0.3 mL) was heated at 135~180° C. for 10 min. Preparative HPLC purification gave compound A-63 as the acetate salt. Compounds A-77 to A-80 were also prepared from compound A47, *mutatis mutandis*.

EXAMPLE K

Compound A-58. Still referring to FIG. 9, a solution of compound A-47 hydrochloride (50 mg) in DMF (2 mL) and DIEA (0.1 mL) was treated with $BrCH_2CN$ (0.1 mL) and stirred at RT for 10 min. HPLC purification of the crude mixture gave compound A-58 as the acetate salt.

EXAMPLE L

Figure 10:
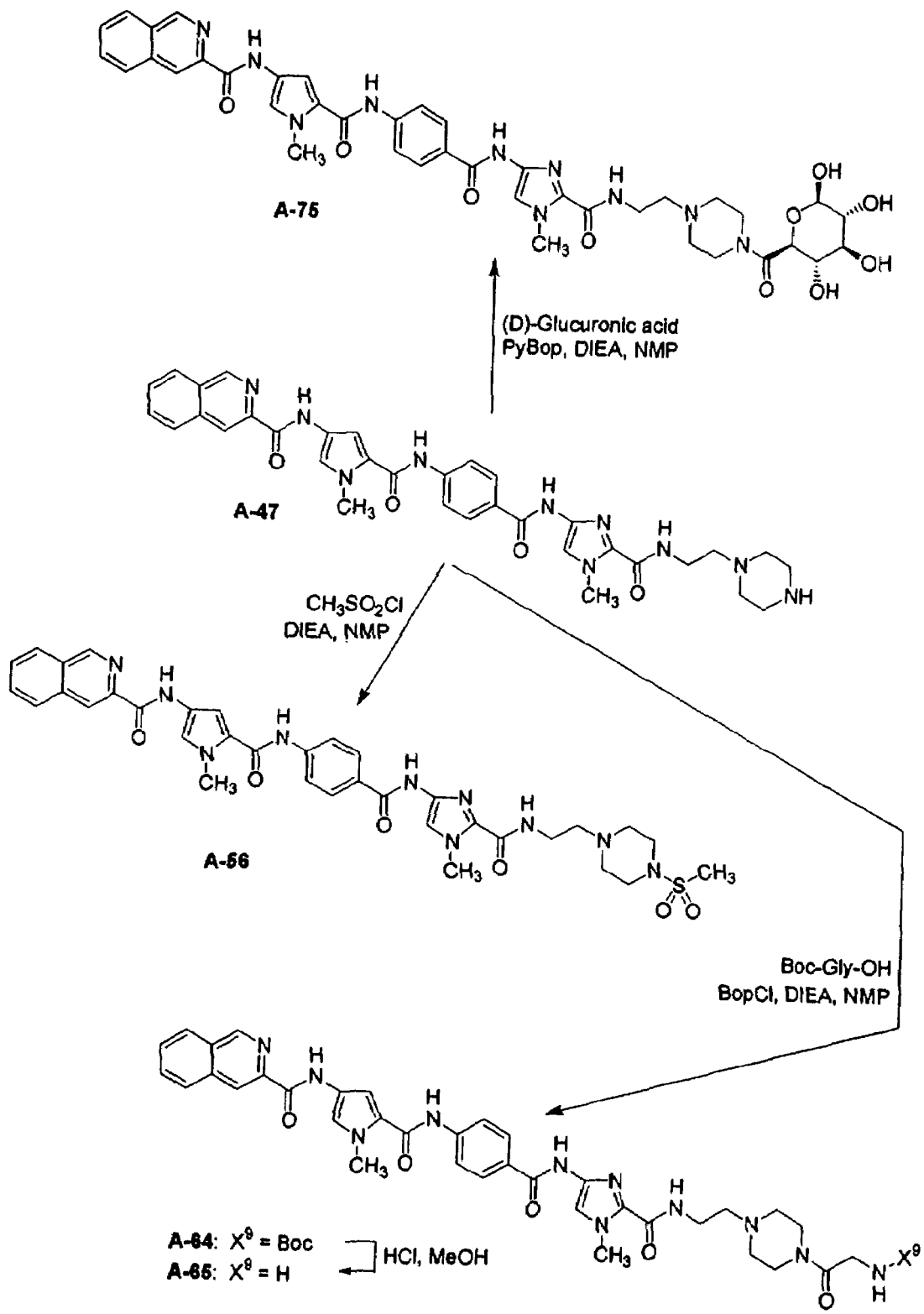

Compound A-75. Compound A-47 can serve as the precursor for the synthesis of other compounds of this invention, as illustrated in FIG. 10. A solution of compound A-47 hydrochloride (137 mg) and (D)-glucuronic acid (77 mg) in NMP (10 mL) and DIEA (1.0 mL) was treated with PyBop (230 mg) and stirred at 60° C. for 12 h. HPLC purification of the crude mixture gave compound A-75 as the acetate salt.

EXAMPLE M

Compound A-56. Still referring to FIG. 10, a solution of compound A-47 hydrochloride (50 mg) in NMP (5 mL) and DIEA (1.0 mL) was treated with $CH_3SO_2Cl$ (50 mg) and stirred at RT for 30 min. HPLC purification of the crude mixture gave compound A-56 as the acetate salt.

EXAMPLE N

Compounds A-64 and A-65. Still referring to FIG. 10, a solution of Boc-Gly-OH (114 mg, 0.65 mmol) and BopCl (165 mg, 0.65 mmol) in NMP (2 mL) was treated with DIEA (167 mg, 1.3 mmol) and DMAP (16 mg, 0.13 mmol), stirred at RT for 30 min, and treated with a solution of compound A-47 hydrochloride (360 mg, 0.5 mmol) in NMP (1 mL) and DIEA (0.5 mL). The mixture was stirred at 60° C. for 30 min and poured into 40 mL stirring ice-water. The resulting precipitate was collected by filtration, washed with $H_2O$ (2×20 mL) and dried by lyophilization to give compound (170 mg, 43% yield). A solution of compound A-64 (130 mg) in MeOH (10 mL) was treated at RT with a stream of anhydrous HCl gas for 2 min. Addition of $Et_2O$ (40 mL) gave a precipitate, which was collected by filtration and dried to afford compound A-65 as the hydrochloride salt.

EXAMPLE O

Figure 11:
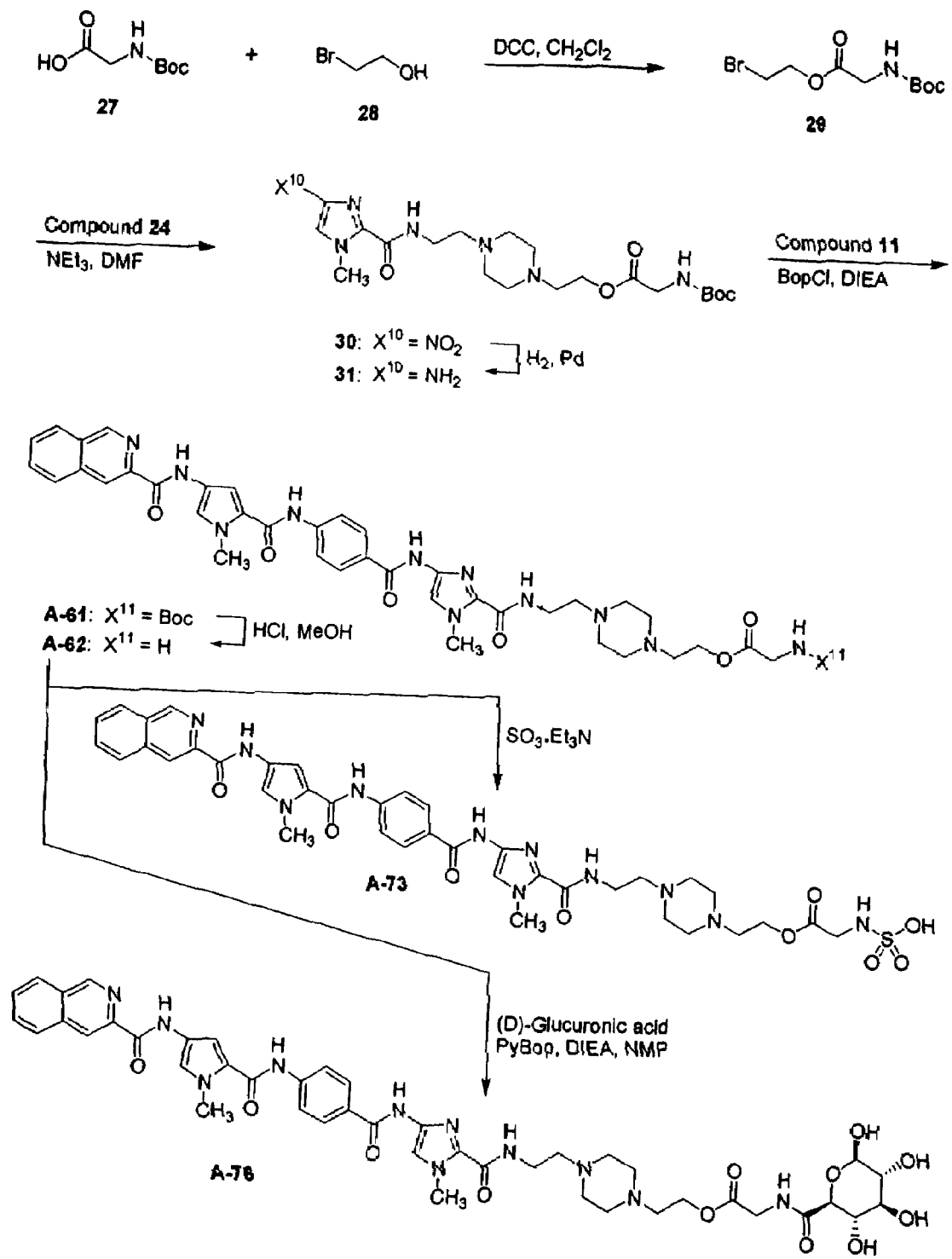

Compounds A-61 and A-62. Referring to FIG. 11, at 0° C., DCC (2.06 g, 10 mmol) and DMAP (122 mg, 1 mmol) was added to a solution of Boc-Gly-OH 27 (1.75 g, 10 mmol) and 2-bromoethanol 28 (1.24 g, 10 mmol) in $CH_2Cl_2$ (20 mL). The mixture was stirred at 0° C. for 30 min and the resulting precipitate removed by filtration. The filtrate was concentrated to give crude intermediate 29, which was used for next reaction without further purification. A solution of intermediate 29 in DMF (100 mL) was treated with nitro intermediate 24 (2.8 g, 10 mmol) and $NEt_3$ (1.01 g, 10 mmol), stirred at 60° C. for 12 h, and treated with AcOEt (200 mL). The organic phase was washed with $H_2O$ (3×100 mL) and brine and dried ($Na_2SO_4$). Evaporation of the solvent and purification of the crude material by column chromatography ($SiO_2$) gave Boc-protected compound 30 (1.2 g). Pd-catalyzed hydrogenation of compound 30 gave compound 31. Coupling of 31 with carboxylic acid 11 was performed following the procedure of Example C to give compound A-61. Deprotection of compound A-61 in saturated HCl/MeOH solution gave compound A-62 as the hydrochloride salt.

EXAMPLE P

Figure 13:
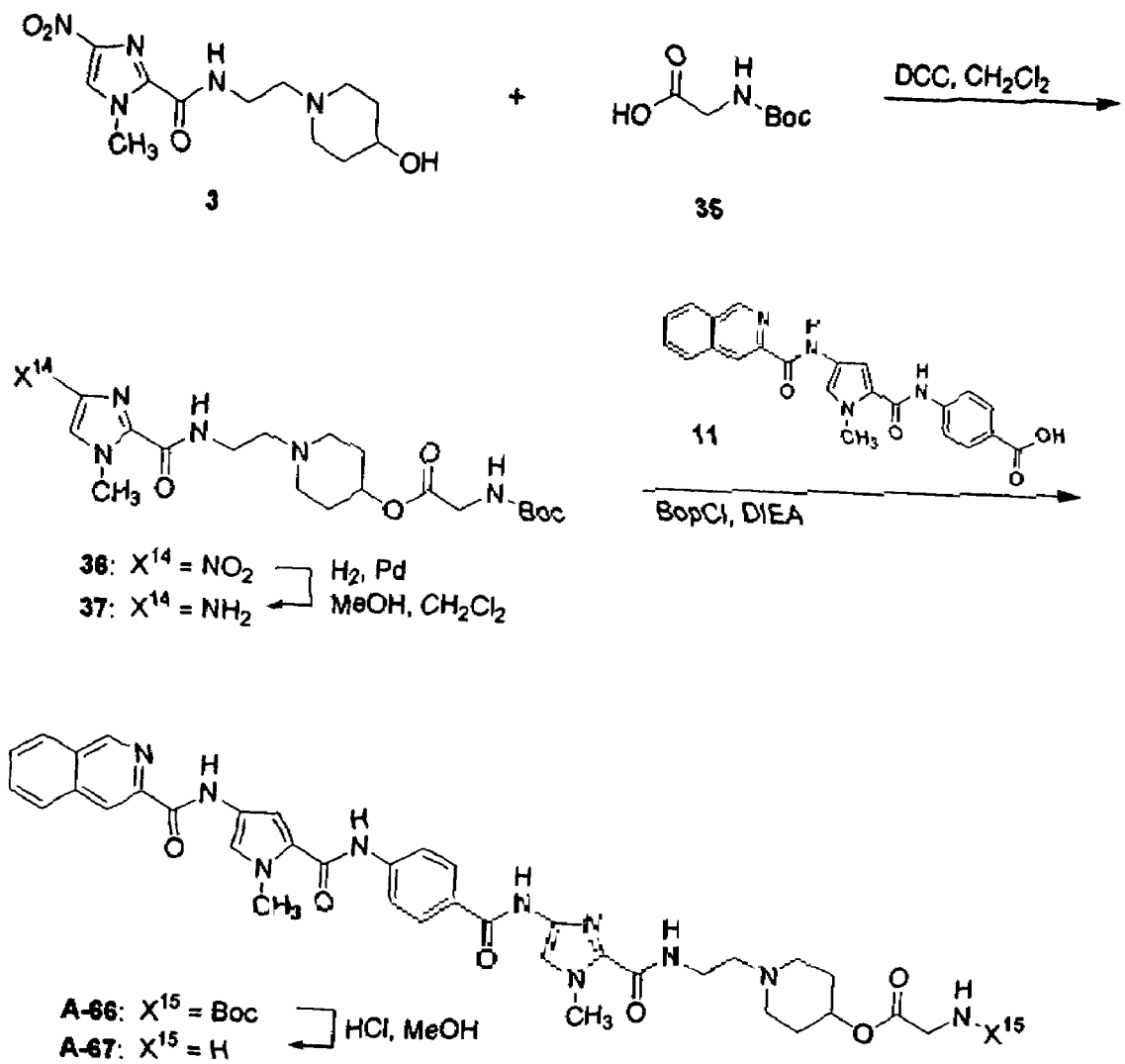

Compounds A-66 and A-67. Referring to FIG. 13, compounds A-66 and A-67 were synthesized from compounds 3 and 35 following the procedure described in Example O.

EXAMPLE Q

Compound A-68. A mixture of compound A-66 (100 mg), $SO_3.NEt_3$, NMP (4 mL) and DIEA (0.2 mL) was stirred at 140° C. for 2 min, cooled to RT, treated with 30 mL of $H_2O$, and acidified to pH=4 using an aqueous 1M HCl solution. The resulting precipitate was collected by centrifugation and washed with $H_2O$ (2×30 mL) to give compound A-68.

EXAMPLE R

Compounds A-73 and A-76. Returning to FIG. 11, compound A-62 can serve as the precursor for other compounds of this invention. Reaction of compound A-62 and sulfur trioxide-triethylamine complex using the procedure in Example Q yielded compound A-73. Reaction of compound A-62 and (D)-glucuronic acid following the procedure of Example L gave compound A-76.

EXAMPLE S

Compound A-74. Compound A-74 was prepared from compound A-66 and (D)-glucuronic acid using the procedure of Example L.

EXAMPLE T

Figure 12:
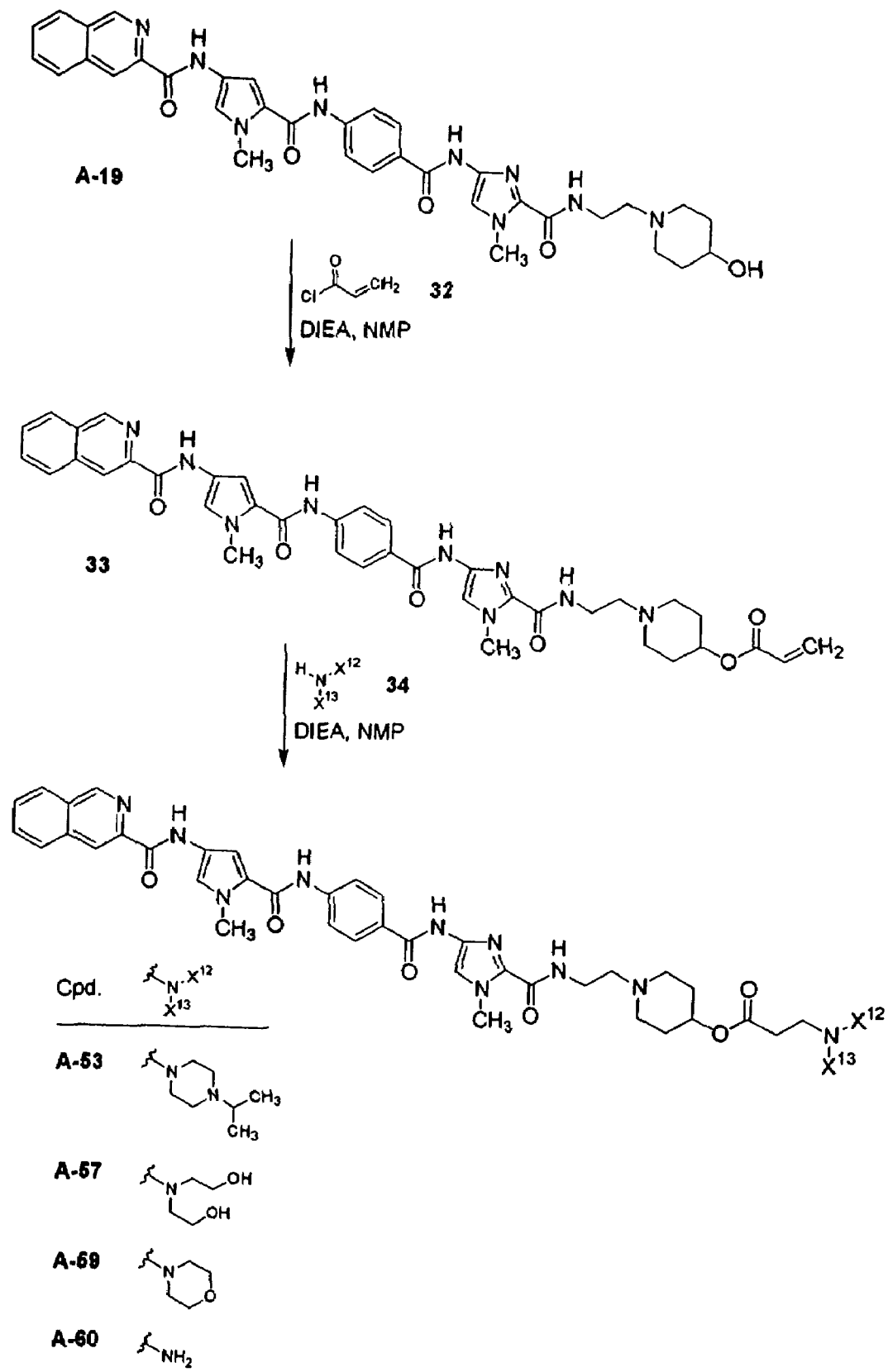

Compounds A53, A-57, A-59. and A-60. Referring to FIG. 12, a solution of compound A-19 (200 mg) in NMP (5 mL) was treated at RT with DIEA (0.1 mL) and acryloyl chloride 32 (100 mg). The mixture was stirred at RT for 10 min and diluted with AcOEt (20 mL). The resulting precipitate was collected by filtration, washed with $Et_2O$, and dried to give intermediate 33. A solution of intermediate 33 (50 mg) in NMP (2 mL) was treated at RT with N-isopropylpiperazine (0.5 mL) and stirred at 60° C. for 30 min. The crude product was purified by HPLC to give compound A-53. Compounds A-57, A-59, and A-60 were also made by this general approach, *mutatis mutandis*, by using appropriate amines 34.

EXAMPLE U

Compound A-7. Compound A-7 was prepared from compound A-8 by Pd-catalyzed hydrogenation in MeOH, followed by purification by HPLC.

In Vitro Biological Activity—Minimum Inhibitory Concentrations

In vitro biological activity data were collected for a variety of microorganisms, including *Staphylococcus aureus* (ATCC 27660, a methicillin resistant strain (MRSA); ATCC 13709, a methicillin sensitive strain (MSSA)), *Enterococcus faecalis* (ATCC 29212), *Bacillus cereus* (ATCC 11778), *Streptococcus pneumoniae* (ATCC 49619), *Candida albicans* (ATCC 38247), *Escherichia coli* (ATCC 25922), and *Moraxella* (now *Branhamella*) *catarrhalis* (ATCC 25238). It is noteworthy that some compounds of this invention exhibit activity against the Gram-negative bacterium *E. coli*, a trait not commonly found among poly(heteroaromatic carboxamide) antimicrobial agents.

Preferably, compounds of this invention have a minimum inhibitory concentration of 4 μg/mL or less against at least one of *Staphylococcus aureus* (ATCC 27660), *Streptococcus pneumoniae* (ATCC 49619), and *Enterococcus faecium* (ATCC 29212).

The minimal inhibition concentration (MIC) of these compounds was determined using the National Committee for Clinical Laboratory Standards (NCCLS) broth microdilution assay in microtiter plates, as set forth in: (1) the guidelines of the National Committee for Clinical Laboratory Standards (NCCLS) Document M7-A4 (NCCLS, 1997); (2) the guidelines of the National Committee for Clinical Laboratory Standards (NCCLS) Document M11-A4 (NCCLS, 1997); and (3) the guidelines and reference method of the National Committee for Clinical Laboratory Standards (NCCLS) Document M27-T (NCCLS, 1995). For antifungal assays, the method recommended in Murray, P R., 1995 *Manual of Clinical Microbiology* (ASM Press, Washington, DC.), was employed.

The results are presented in Table B below, which is keyed as follows:

Organism tested against:

A = *S. aureus* ATCC 13709
B = *S. aureus* ATCC 27660
C = *E. faecalis* ATCC 29212
D = *B. cereus* ATCC 11778
E = *S. pneumoniae* ATCC 49619
F = *C. albicans* ATCC 38247
G = *E. coli* ATCC 25922
H = *M. catarrhalis* (ATCC 25238)
Activity:

+++ = MIC ≦ 4 μg/mL
++ = 4 < MIC < 12 μg/mL
+ = 12 ≦ MIC ≦ 32 μg/mL
>32 = MIC greater than 32 μg/mL

TABLE B

Organism (Minimum Inhibitory Concentration (MIC), μg/mL)

| Ref. No. | A | B | C | D | E | F | G | H |
|---|---|---|---|---|---|---|---|---|
| A-1 | +++ | +++ | +++ | +++ | +++ | >32 | >32 | + |
| A-2 | +++ | +++ | +++ | +++ | +++ | >32 | >32 | + |
| A-3 | +++ | +++ | +++ | +++ | +++ | >32 | >32 | ++ |
| A-4 | +++ | +++ | +++ | +++ | +++ | + | ++ | +++ |
| A-5 | +++ | +++ | +++ | +++ | +++ | >32 | >32 | >32 |
| A-6 | +++ | +++ | +++ | +++ | +++ | + | + | ++ |
| A-7 | +++ | +++ | +++ | +++ | +++ | >32 | >32 | + |
| A-8 | +++ | +++ | +++ | +++ | +++ | ++ | ++ | ++ |
| A-9 | +++ | +++ | +++ | +++ | +++ | ++ | ++ | + |
| A-10 | +++ | +++ | +++ | +++ | +++ | >32 | >32 | +++ |
| A-11 | +++ | +++ | +++ | +++ | +++ | >32 | >32 | +++ |
| A-12 | +++ | +++ | +++ | +++ | +++ | >32 | >32 | +++ |
| A-13 | +++ | +++ | +++ | +++ | +++ | >32 | >32 | +++ |
| A-14 | +++ | +++ | +++ | +++ | +++ | >32 | >32 | +++ |
| A-15 | +++ | +++ | +++ | +++ | +++ | >32 | >32 | +++ |
| A-16 | +++ | +++ | +++ | +++ | +++ | >32 | +++ | +++ |
| A-17 | +++ | +++ | +++ | +++ | +++ | + | +++ | +++ |
| A-18 | +++ | +++ | +++ | +++ | +++ | >32 | >32 | +++ |
| A-19 | +++ | +++ | +++ | +++ | +++ | >32 | + | +++ |
| A-20 | +++ | +++ | +++ | +++ | +++ | + | +++ | +++ |
| A-21 | +++ | +++ | +++ | +++ | +++ | >32 | >32 | +++ |
| A-22 | +++ | +++ | +++ | +++ | +++ | >32 | >32 | +++ |
| A-23 | +++ | +++ | +++ | +++ | +++ | >32 | >32 | +++ |
| A-24 | +++ | +++ | +++ | +++ | +++ | ++ | >32 | +++ |
| A-25 | +++ | +++ | +++ | +++ | +++ | >32 | >32 | +++ |
| A-26 | +++ | +++ | +++ | +++ | +++ | >32 | >32 | >32 |
| A-27 | +++ | +++ | +++ | +++ | +++ | >32 | >32 | +++ |
| A-28 | +++ | +++ | +++ | +++ | +++ | + | ++ | +++ |
| A-29 | +++ | +++ | +++ | +++ | +++ | + | ++ | +++ |
| A-30 | +++ | +++ | +++ | +++ | +++ | >32 | >32 | + |
| A-31 | +++ | +++ | ++ | ++ | +++ | + | >32 | >32 |
| A-32 | +++ | +++ | +++ | +++ | +++ | >32 | >32 | +++ |
| A-33 | +++ | +++ | +++ | +++ | +++ | >32 | +++ | >32 |
| A-34 | +++ | +++ | +++ | +++ | +++ | >32 | +++ | +++ |
| A-35 | +++ | +++ | +++ | +++ | +++ | >32 | >32 | ++ |
| A-36 | +++ | +++ | +++ | +++ | +++ | + | >32 | ++ |
| A-37 | +++ | +++ | +++ | +++ | +++ | >32 | +++ | +++ |
| A-38 | +++ | +++ | +++ | +++ | +++ | >32 | >32 | +++ |
| A-39 | +++ | +++ | +++ | +++ | +++ | >32 | >32 | >32 |
| A-40 | +++ | +++ | +++ | +++ | +++ | >32 | >32 | ++ |
| A-41 | +++ | +++ | +++ | +++ | +++ | >32 | >32 | +++ |
| A-42 | +++ | +++ | +++ | ++ | + | + | >32 | >32 |
| A-43 | +++ | +++ | +++ | +++ | +++ | >32 | >32 | >32 |
| A-45 | +++ | +++ | +++ | +++ | +++ | >32 | >32 | + |
| A-46 | +++ | +++ | +++ | +++ | +++ | >32 | >32 | ++ |
| A-47 | +++ | +++ | +++ | +++ | +++ | + | >32 | +++ |
| A-48 | +++ | +++ | +++ | +++ | +++ | >32 | >32 | +++ |
| A-49 | +++ | +++ | + | >32 | +++ | >32 | >32 | >32 |
| A-50 | +++ | +++ | ++ | + | +++ | >32 | >32 | >32 |
| A-51 | +++ | +++ | +++ | +++ | +++ | >32 | >32 | +++ |
| A-52 | >32 | ++ | >32 | >32 | >32 | >32 | >32 | >32 |
| A-53 | +++ | +++ | +++ | +++ | +++ | >32 | >32 | +++ |
| A-54 | +++ | +++ | +++ | +++ | +++ | >32 | >32 | >32 |

TABLE B-continued

Organism (Minimum Inhibitory Concentration (MIC), µg/mL)

| Ref. No. | A | B | C | D | E | F | G | H |
|---|---|---|---|---|---|---|---|---|
| A-55 | +++ | +++ | +++ | +++ | +++ | >32 | >32 | + |
| A-56 | +++ | +++ | +++ | +++ | +++ | >32 | >32 | +++ |
| A-57 | +++ | +++ | +++ | +++ | +++ | >32 | ++ | +++ |
| A-58 | +++ | +++ | +++ | +++ | +++ | >32 | >32 | +++ |
| A-59 | +++ | +++ | +++ | +++ | +++ | >32 | >32 | +++ |
| A-60 | +++ | +++ | +++ | +++ | +++ | ++ | >32 | ++ |
| A-61 | +++ | +++ | +++ | +++ | +++ | >32 | >32 | +++ |
| A-62 | +++ | +++ | +++ | +++ | +++ | >32 | >32 | +++ |
| A-63 | +++ | +++ | +++ | +++ | +++ | >32 | +++ | +++ |
| A-64 | +++ | +++ | +++ | +++ | +++ | >32 | >32 | ++ |
| A-65 | +++ | +++ | +++ | +++ | +++ | ++ | >32 | +++ |
| A-66 | +++ | +++ | +++ | +++ | +++ | >32 | >32 | +++ |
| A-67 | +++ | +++ | +++ | +++ | +++ | ++ | + | +++ |
| A-68 | +++ | +++ | +++ | +++ | + | >32 | >32 | >32 |
| A-69 | +++ | +++ | +++ | +++ | +++ | >32 | >32 | +++ |
| A-70 | +++ | +++ | +++ | +++ | +++ | >32 | +++ | +++ |
| A-71 | +++ | +++ | +++ | +++ | +++ | >32 | +++ | +++ |
| A-72 | +++ | +++ | +++ | +++ | +++ | >32 | >32 | +++ |
| A-73 | +++ | +++ | +++ | +++ | +++ | >32 | >32 | >32 |
| A-74 | +++ | +++ | +++ | +++ | +++ | >32 | >32 | >32 |
| A-75 | +++ | +++ | +++ | +++ | +++ | >32 | >32 | >32 |
| A-76 | +++ | +++ | +++ | +++ | +++ | >32 | >32 | +++ |
| A-77 | +++ | ++ | +++ | +++ | +++ | >32 | >32 | + |
| A-78 | +++ | +++ | +++ | +++ | +++ | >32 | + | +++ |
| A-79 | +++ | +++ | +++ | +++ | +++ | >32 | >32 | + |
| A-80 | +++ | +++ | +++ | +++ | +++ | >32 | >32 | +++ |
| A-81 | +++ | +++ | +++ | +++ | +++ | >32 | >32 | +++ |

In Vitro Biological Activity—Diffusion Analysis

The diffusion assays on a compound of this invention were performed according to NCCLS Guidelines (Performance Standards for Antimicrobial Susceptibility Testing, M100-S12 vol. 22 and Performance Standards for Antimicrobial Disk Susceptibility Tests, M2-A7 vol. 20) with the following modifications:

1. Disk Diffusion of Formulated Creams: A sterile filter paper disk was wet with 0.85% sodium chloride and cream was applied to one side of the disk. The disk was placed, cream side down, on the agar (tryptic soy agar, or TSA).

2. Diffusion of Formulated Creams from Wells with 1.2% Cation-Adjusted Mueller Hinton Agar (CAMHA) Overlay: Glass cylinders were used to create wells in an 15 ml overlay of 1.2% CAMHB containing the test microorganism. Cream was applied to the wells.

Generally, diffusion of the drug from the inoculation site (the disk or the well, as the case may be) through the agar creates a concentration gradient of the test compound. Bacterial growth is inhibited by the drug, creating a zone of inhibition. A larger inhibition zone corresponds to a more active compound.

The activity of the compound was determined by measurement of the zone of inhibition surrounding the disk. The results are provided in Tables C, D, and E. The diffusion results of Table C measure the diffusion of free compound. The diffusion results of Tables D and E measure the diffusion of compound formulated into a cream.

TABLE C

Disc Diffusion of Non-formulated Compounds

Zone Diameter (nearest whole mm)

| Compound (30 µg/disc) | Staphylococcus aureus ATCC 13709 on TSA | Enterococcus faecalis ATCC 29212 on TSA + 5% Sheep Blood | Streptococcus pneumoniae ATCC 49619 on TSA + 5% Sheep Blood |
|---|---|---|---|
| 13873 * | 9 | 7 | 9 |
| Vancomycin | 15 | 15 | 19 |

(6.3 mm is the diameter of the disc, indicating no inhibition zone/diffusion.)
* Precipitation of compound observed after 1:6 dilution in sterile water.

TABLE D

Disc Diffusion of Formulated Creams

| Compound (20 L saline, then cream applied to disc) | Zone Diameter (nearest whole mm) | |
|---|---|---|
| | Staphylococcus aureus ATCC 13709 on TSA | Staphylococcus epidermidis ATCC 12228 on TSA |
| 13873 | 9 | 13 |
| 3-in-1 Antibiotic Ointment * | 9 | 16 |

(6.3 mm is the diameter of the disc, indicating no inhibition zone/diffusion.)
* Contained bacitracin, neomycin, and polymyxin B

TABLE E

Disc Diffusion of Formulated Creams from Wells in 1.2% CAMHA Overlay

Zone Diameter (nearest whole mm)

| Compound | Staphylococcus aureus ATCC 13709 on TSA | Staphylococcus epidermidis ATCC 12228 on TSA |
|---|---|---|
| 13873 | 14 | 17 |

(8 mm is the diameter of the well indicating no inhibition zone/diffusion)

The above results demonstrate that the tested compound has the diffusion properties needed for use as a topical antibiotic.

In Vivo Biological Activity

This example demonstrates in vivo efficacy against infection by methicillin resistant *Staphylococcus aureus* ATCC 33591, using a murine neutropenic thigh model.

A *S. aureus* ATCC 33591 culture was grown to log phase overnight and diluted in phosphate buffered saline (pH 7.4) to an optical density of about 0.1 at 600 nm, giving an approximate concentration of $10^8$ cfu/mL. The suspension was diluted 1:100 in phosphate buffered saline (pH 7.4) for a final concentration of $10^6$ cfu/mL.

Outbred female ICR mice (approx. 25 gram body weight) were rendered neutropenic by treatment with cyclophosphamide (200 mg/kg body weight, intraperitoneal injection) at 1 and 4 days prior to inoculation. Groups of 3-5 mice were inoculated with 0.05 mL of the bacteria (approx. $10^6$ cfu/mL) into the anterior thigh. Each group was treated intravenously two hours post infection with vehicle or test compound. The mice were sacrificed at predetermined time-points (e.g. 5 or 24 hrs) after treatment and thighs were collected aseptically. Each thigh was placed into sterile saline, and homogenized. The tissue homogenates were diluted appropriately for plating on agar plates. Colony counts were recorded (cfu/thigh) and compared to control groups. The data are presented in Table F below:

TABLE F

Murine Neutropenic Thigh Model

| Compound No. (Time) | Dose (mg/kg) | Colony Count (log cfu/gram) | |
|---|---|---|---|
| | | Compound | Vehicle |
| 13873 (5 hrs) | 25 | 4.10 | 7.16 |
| 13873 (24 hrs) | 30 | 4.24 | 7.11 |
| 13781 (5 hrs) | 40 | 5.95 | 7.45 |
| 13781 (5 hrs) | 20 | 6.50 | 7.45 |
| 13876 (5 hrs) | 50 | 6.29 | 7.28 |
| 13881 (5 hrs) | 50 | 6.22 | 7.28 |
| 13874 (5 hrs) | 50 | 6.42 | 7.28 |

In vivo efficacy was shown by a decrease in colony count (log cfu/gram of tissue) in the compound-treated animals when compared against the colony count in animals given only the vehicle.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A compound selected from the group consisting of A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, A-50, A-51, A-52, A-53, A-54, A-55, A-56, A-57, A-58, A-59, A-60, A-61, A-62, A-63, A-64, A-65, A-66, A-67, A-68, A-69, A-70, A-71, A-72, A-73, A-74, A-75, A-76, A-77, A-78, A-79, A-80 and A-81, each compound having Formula I:

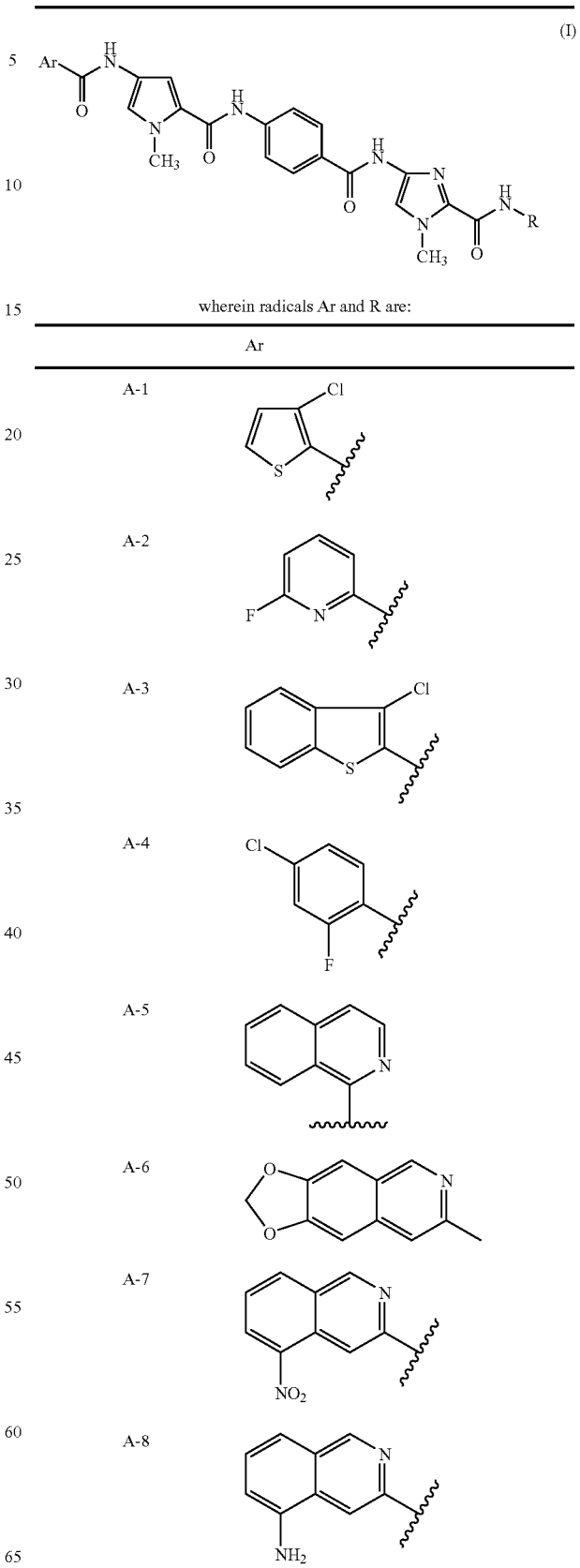

-continued
(I)
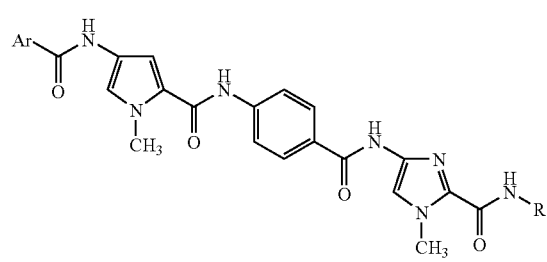
wherein radicals Ar and R are:
A-9 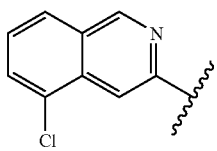
A-10 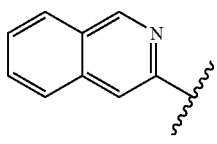
A-11 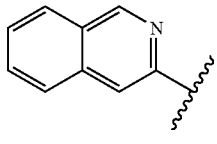
A-12 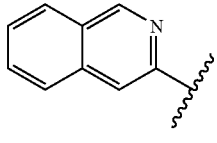
A-13 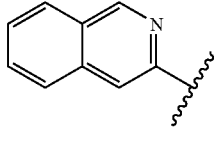
A-14 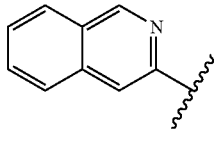
A-15 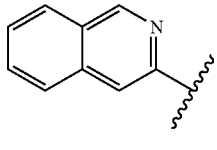
A-16 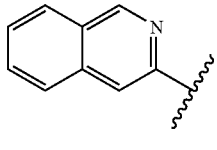
-continued
(I)
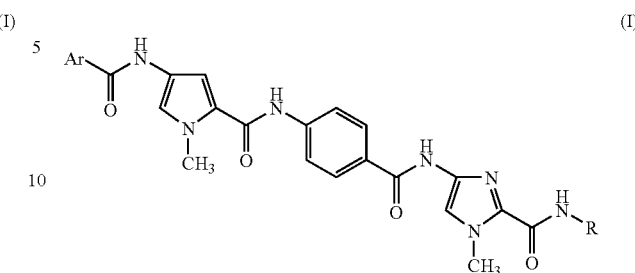
wherein radicals Ar and R are:
A-17 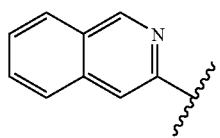
A-18 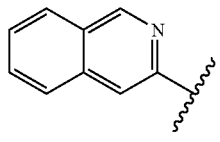
A-19 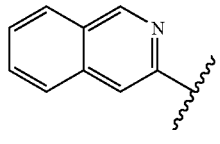
A-20 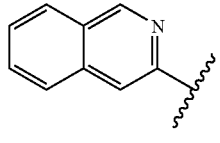
A-21 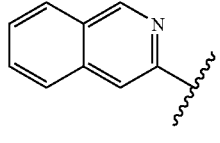
A-22 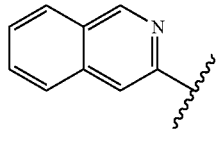
A-23 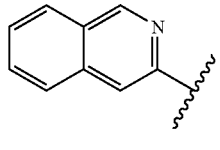
A-24

-continued
(I)
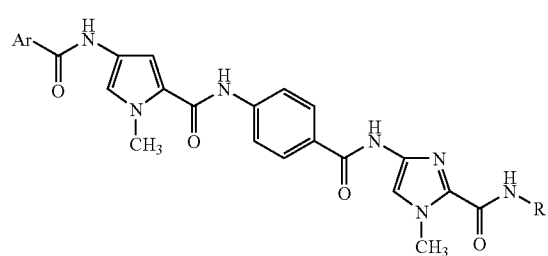
wherein radicals Ar and R are:
A-25 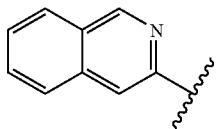
A-26 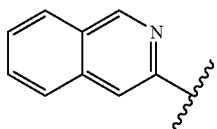
A-27 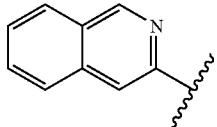
A-28 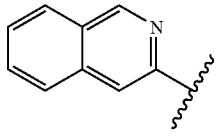
A-29 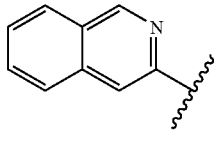
A-30 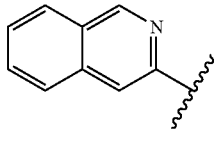
A-31 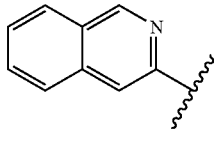
A-32 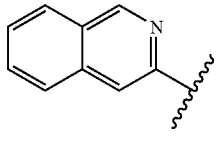
-continued
(I)
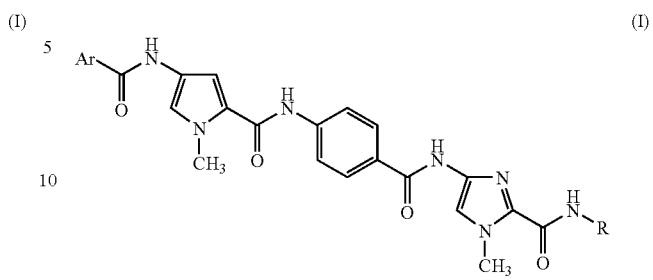
wherein radicals Ar and R are:
A-33 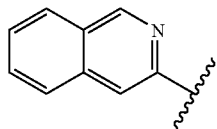
A-34 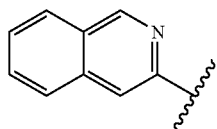
A-35 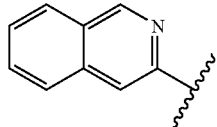
A-36 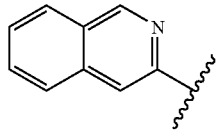
A-37 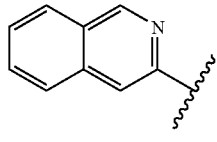
A-38 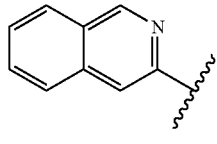
A-39 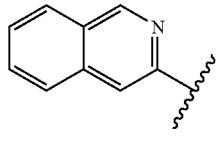
A-40 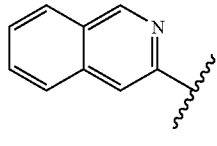

-continued
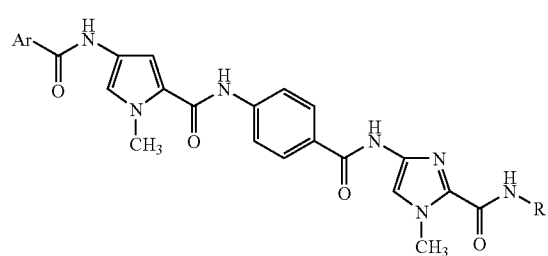 (I)
wherein radicals Ar and R are:
A-41 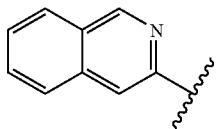
A-42 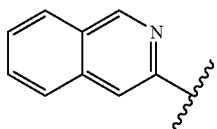
A-43 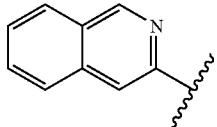
A-44 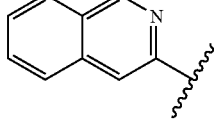
A-45 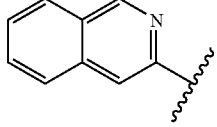
A-46 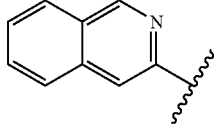
A-47 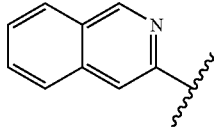
A-48 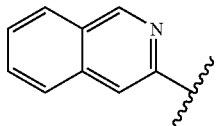
-continued
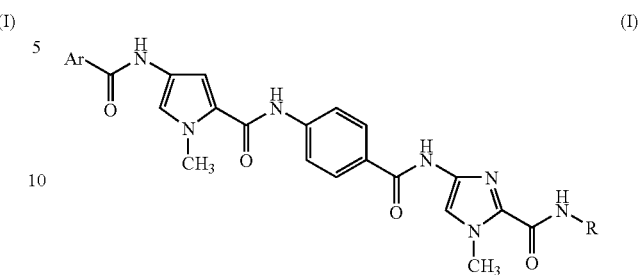 (I)
wherein radicals Ar and R are:
A-49 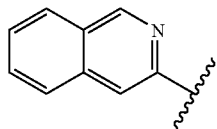
A-50 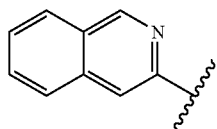
A-51 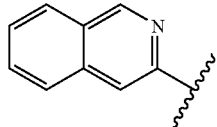
A-52 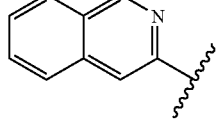
A-53 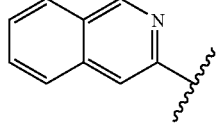
A-54 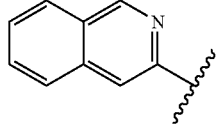
A-55 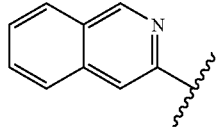
A-56 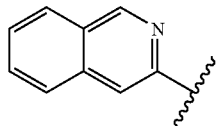

-continued
(I)
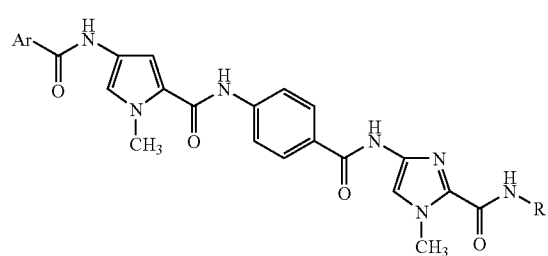
wherein radicals Ar and R are:
A-57 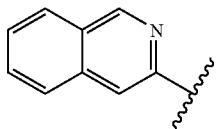
A-58 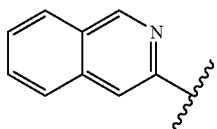
A-59 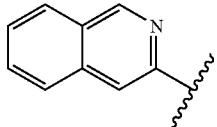
A-60 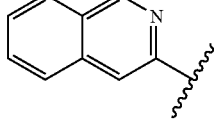
A-61 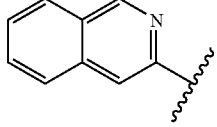
A-62 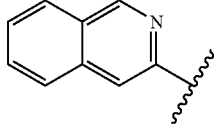
A-63 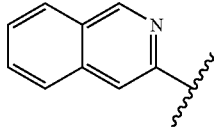
A-64 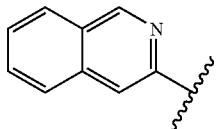
-continued
(I)
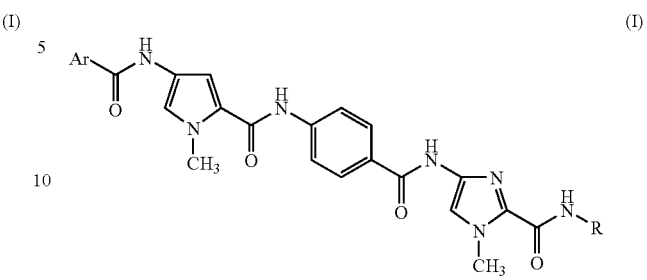
wherein radicals Ar and R are:
A-65 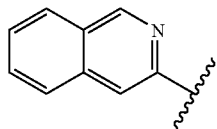
A-66 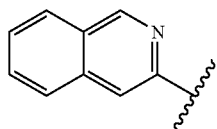
A-67 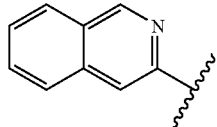
A-68 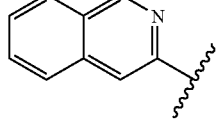
A-69 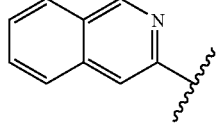
A-70 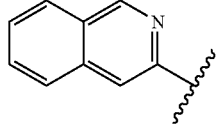
A-71 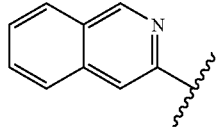
A-72 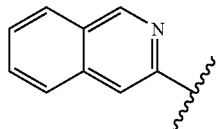

-continued
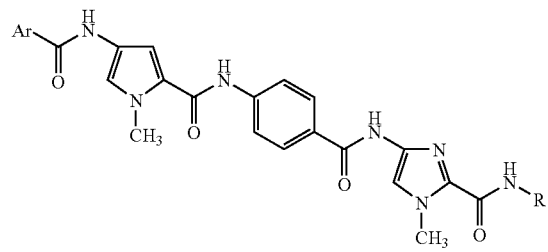
wherein radicals Ar and R are:
A-73 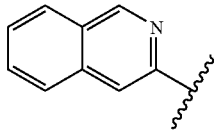
A-74 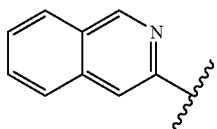
A-75 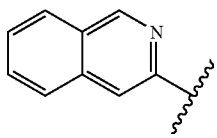
A-76 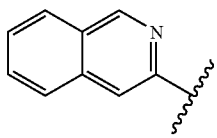
A-77 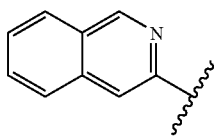
A-78 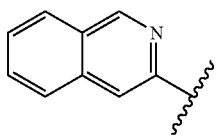
A-79 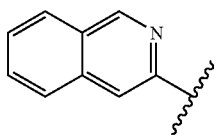
A-80 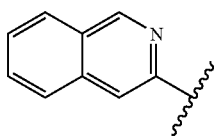
-continued
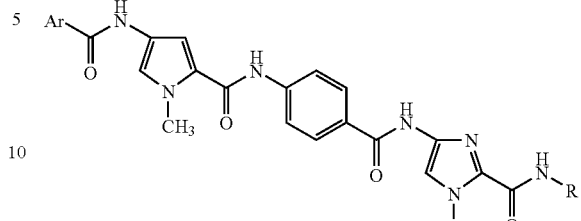
wherein radicals Ar and R are:
A-81 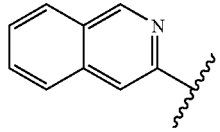
R
A-1 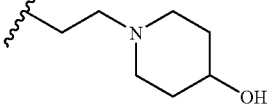
A-2 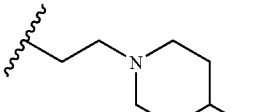
A-3 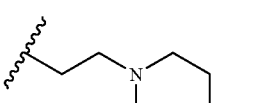
A-4 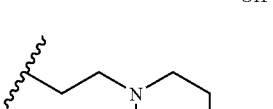
A-5 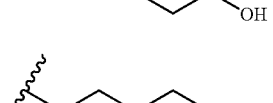
A-6 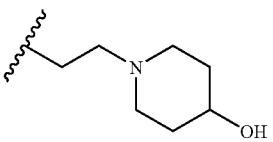
A-7 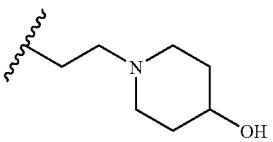

-continued
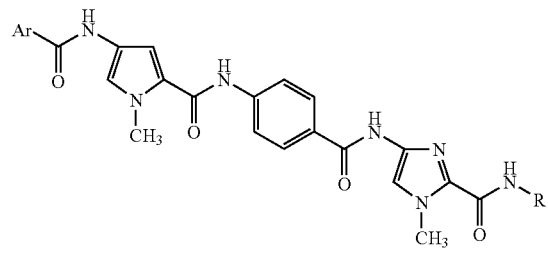
wherein radicals Ar and R are:
A-8 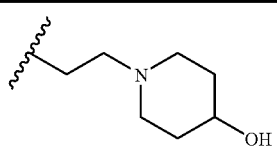
A-9 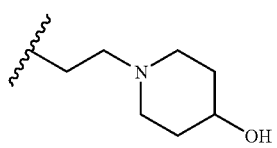
A-10 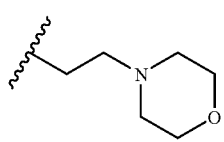
A-11 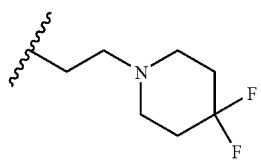
A-12 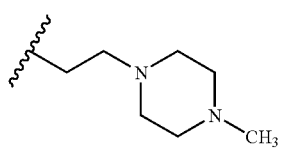
A-13 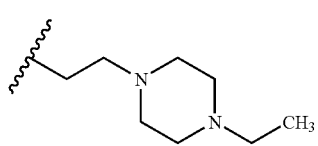
A-14 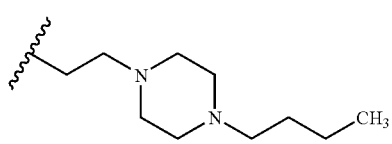
A-15 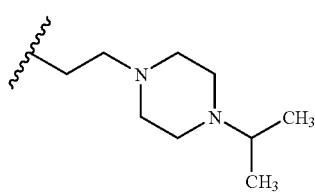
-continued
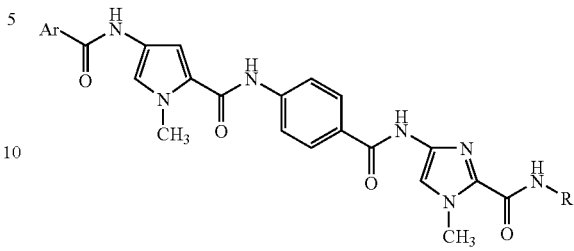
wherein radicals Ar and R are:
A-16 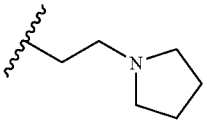
A-17 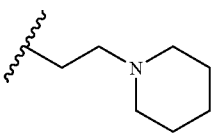
A-18 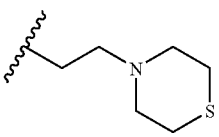
A-19 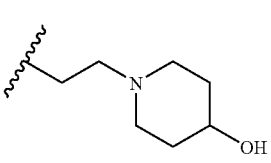
A-20 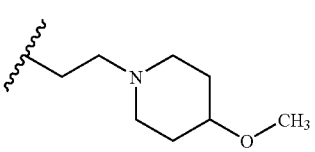
A-21 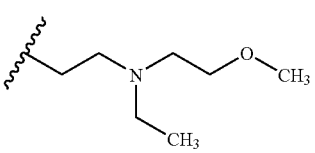
A-22 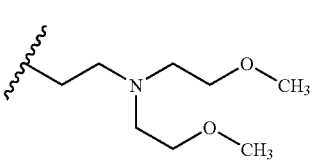
A-23 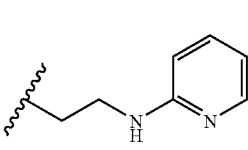

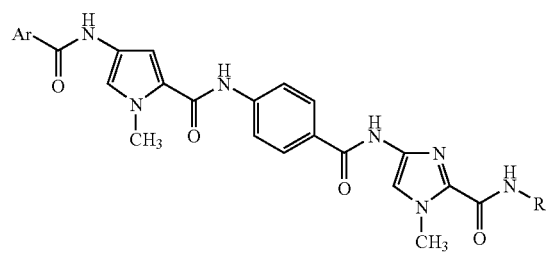
wherein radicals Ar and R are:
A-24 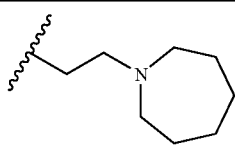
A-25 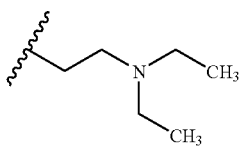
A-26 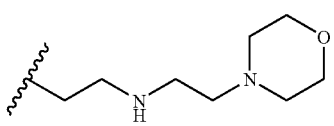
A-27 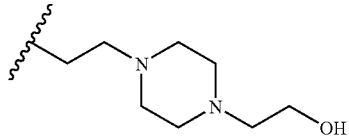
A-28 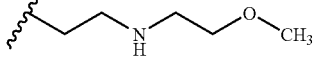
A-29 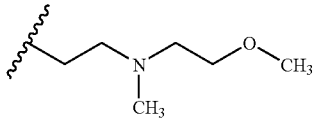
A-30 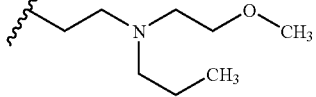
A-31 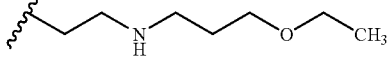
A-32 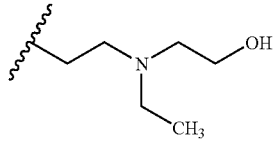
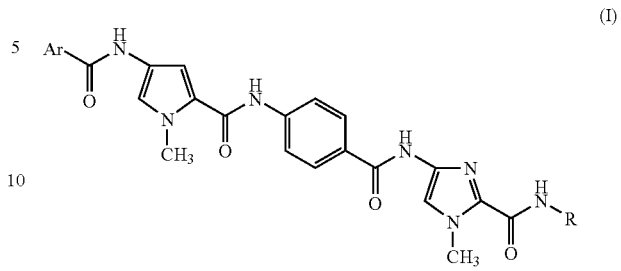
wherein radicals Ar and R are:
A-33 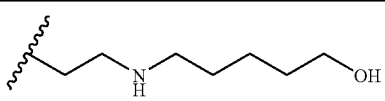
A-34 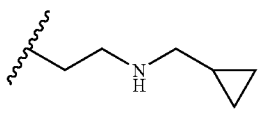
A-35 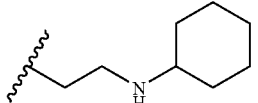
A-36 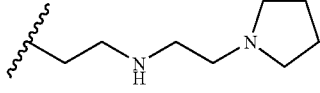
A-37 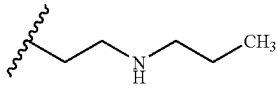
A-38 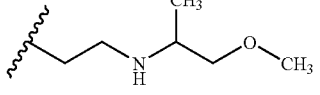
A-39 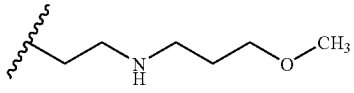
A-40 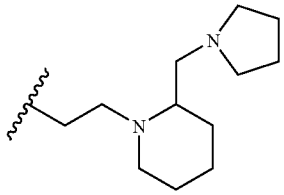
A-41 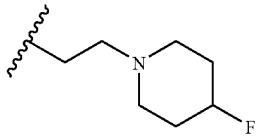
A-42 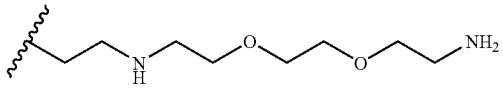

-continued
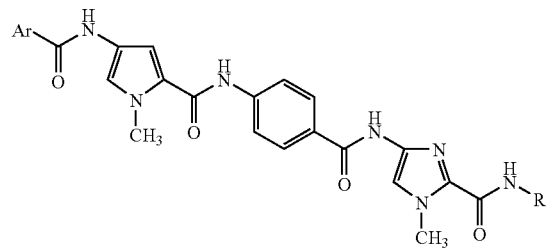
(I)
wherein radicals Ar and R are:
A-43 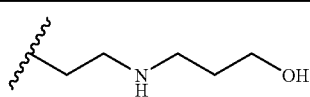
A-44 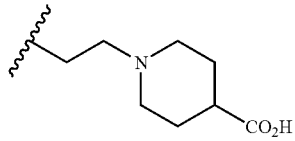
A-45 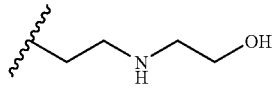
A-46 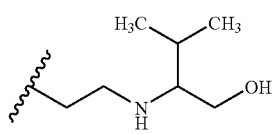
A-47 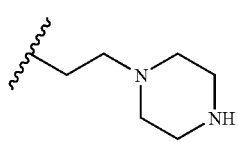
A-48 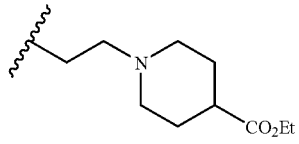
A-49 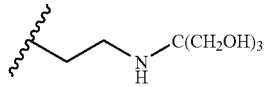
A-50 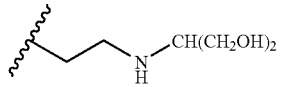
A-51 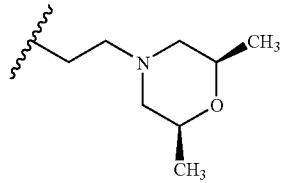
-continued
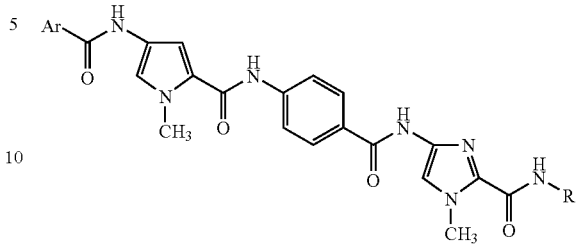
(I)
wherein radicals Ar and R are:
A-52 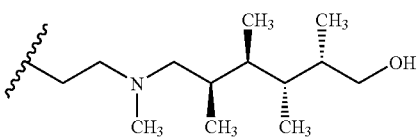
A-53 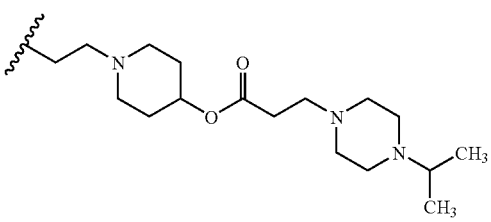
A-54 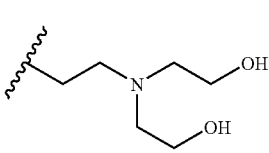
A-55 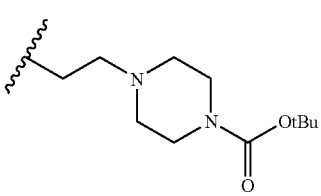
A-56 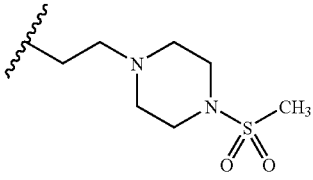
A-57 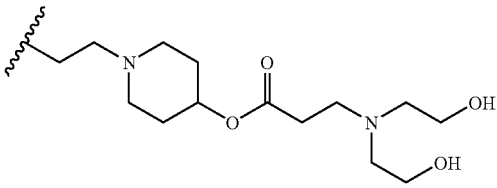
A-58 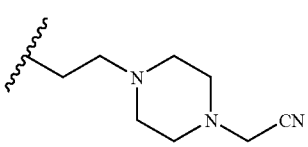

-continued
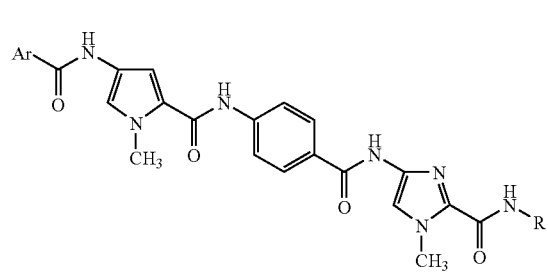
wherein radicals Ar and R are:
A-59 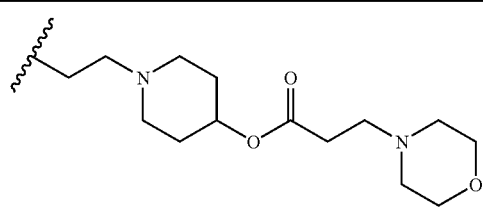
A-60 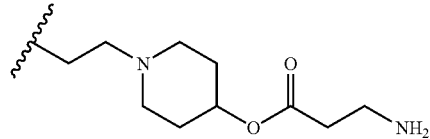
A-61 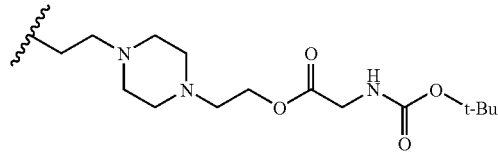
A-62 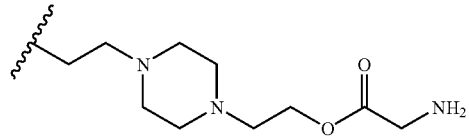
A-63 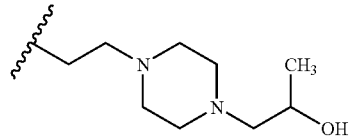
A-64 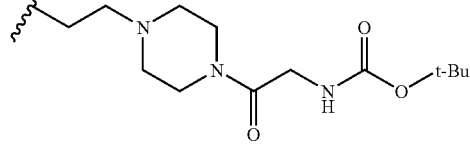
A-65 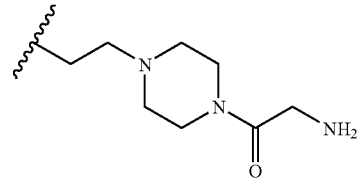
-continued
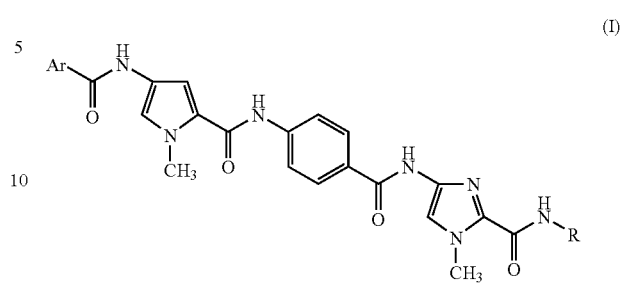
wherein radicals Ar and R are:
A-66 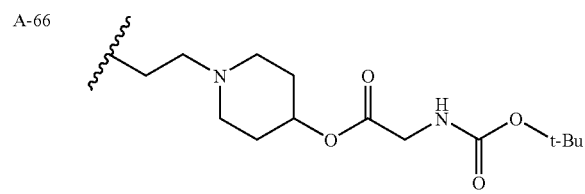
A-67 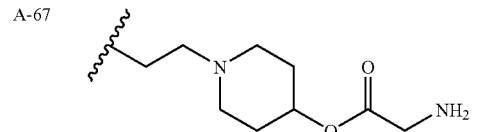
A-68 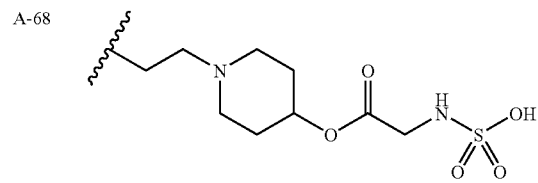
A-69 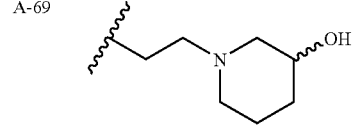
A-70 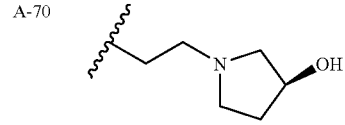
A-71 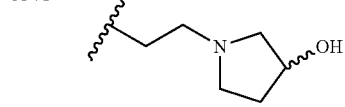
A-72 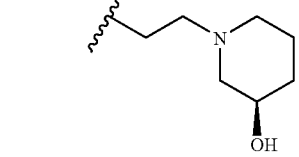

-continued
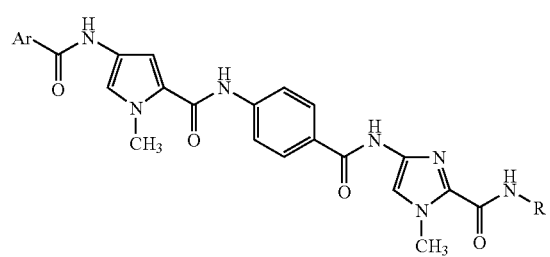
wherein radicals Ar and R are:
A-73 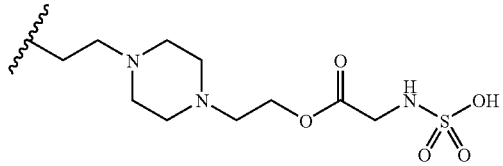
A-74 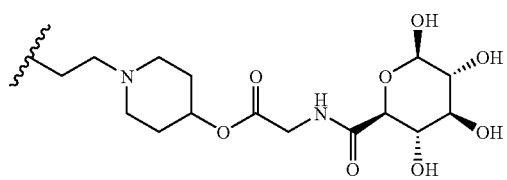
A-75 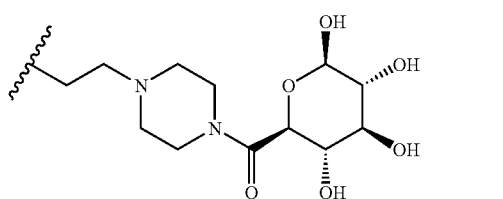
A-76 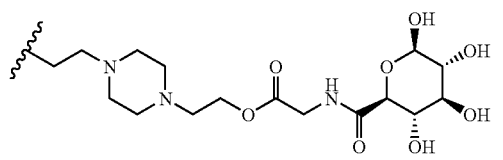
A-77 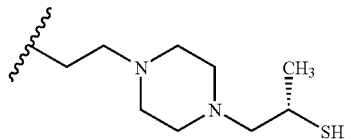
-continued
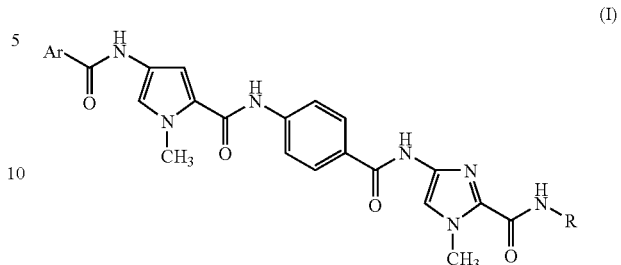
wherein radicals Ar and R are:
A-78 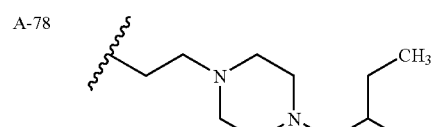
A-79 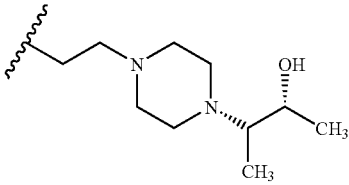
A-80 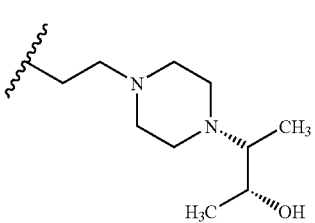
A-81 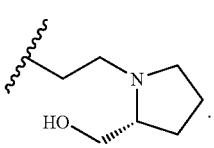
* * * * *